US008962343B2

(12) United States Patent
Ventzki et al.

(10) Patent No.: US 8,962,343 B2
(45) Date of Patent: Feb. 24, 2015

(54) METHOD AND DEVICE FOR PARALLEL ANALYSIS OF BIO MOLECULES

(75) Inventors: Robert Alexander Ventzki, Dossenheim (DE); Josef Stegemann, Heidelberg (DE)

(73) Assignee: Robert Alexander Ventzki, Dossenheim (DE)

( * ) Notice: Subject to any disclaimer, the term of this patent is extended or adjusted under 35 U.S.C. 154(b) by 2118 days.

(21) Appl. No.: 10/506,426

(22) PCT Filed: Mar. 5, 2003

(86) PCT No.: PCT/EP03/02225
§ 371 (c)(1),
(2), (4) Date: Feb. 2, 2005

(87) PCT Pub. No.: WO03/075004
PCT Pub. Date: Sep. 12, 2003

(65) Prior Publication Data
US 2005/0130317 A1 Jun. 16, 2005

(30) Foreign Application Priority Data
Mar. 5, 2002 (DE) .................................. 102 09 609

(51) Int. Cl.
*G01N 1/18* (2006.01)
*G01N 27/447* (2006.01)
*G01N 35/00* (2006.01)

(52) U.S. Cl.
CPC .... *G01N 27/44769* (2013.01); *G01N 27/44721* (2013.01); *G01N 27/44782* (2013.01); *G01N 35/0099* (2013.01)
USPC ........... 436/177; 436/175; 436/178; 422/534; 422/535

(58) Field of Classification Search
USPC ...................... 422/68.1, 69, 78, 82.05, 88, 89, 422/100–102, 527, 534, 535; 436/164, 166, 436/174, 175, 177, 178
See application file for complete search history.

(56) References Cited

U.S. PATENT DOCUMENTS

| | | | |
|---|---|---|---|
| 5,051,162 A | 9/1991 | Kambara et al. | |
| 5,622,819 A | 4/1997 | Herman | |
| 6,120,667 A | 9/2000 | Hayashizaki et al. | |
| 6,410,332 B1 * | 6/2002 | Desrosiers et al. | 436/37 |
| 2002/0168643 A1 | 11/2002 | Wierzbowski et al. | |

FOREIGN PATENT DOCUMENTS

| | | |
|---|---|---|
| WO | WO 99/00664 A | 1/1999 |
| WO | WO 00/73777 A | 12/2000 |
| WO | WO 01/43869 A | 6/2001 |

OTHER PUBLICATIONS

Brenner et al., "Gene expression analysis by massively parallel signature sequencing (MPSS) on microbead arrays," *Nature Biotechnology*, vol. 18, Jun. 2000, pp. 630-634.
Kusukawa et al., "Effect of gelation conditions on the gel structure and resolving power of agarose-based DNA sequencing gels," *Electrophoresis*, vol. 20, 1999, pp. 1455-1461.

* cited by examiner

*Primary Examiner* — Jill Warden
*Assistant Examiner* — Dwayne K Handy
(74) *Attorney, Agent, or Firm* — Foley & Lardner LLP

(57) ABSTRACT

The invention relates to a process and a device for parallel fractionating a multiplicity of individual samples (29) within a 3-dimensional separation medium (6), with the subsequent process steps being carried out:
A first space (2) which extends essentially across all three space coordinates contains the separation medium (6). A multiplicity of individual samples (29) is arranged close to an interface of the first space (2), with the individual samples (29) being arranged essentially in a planar fashion, i.e. their particular center-of-gravity positions are described by two coordinates. Under the influence of one or more physical parameters, the individual samples (29) are able to migrate essentially perpendicularly to the area of their application through the separation medium (6), and are fractionated in the process according to one or more of their properties. Suitable physical parameters are, for example, electric forces (electrophoresis), gravity, diffusion, pressure and concentration gradients and also osmosis or centrifugal forces. The individual samples (29) are detected in selected regions (8) inside or outside the separation medium (6) during their migration (online detection). As an alternative to online detection, data may be received in a 3D manner, after the migration has finished. To this end, an appropriate 3D image-taking process may be used. In the simplest case, the separation medium (6) is cut into disks which are then evaluated by means of a 2D receiving process. In this case, the fractions of the samples are also preparatively accessible. In addition to or alternatively to image-taking, a fraction collector may be attached to an interface of the separation medium (6).

11 Claims, 7 Drawing Sheets

METHOD AND DEVICE FOR PARALLEL ANALYSIS OF BIO MOLECULES

Figure 1:
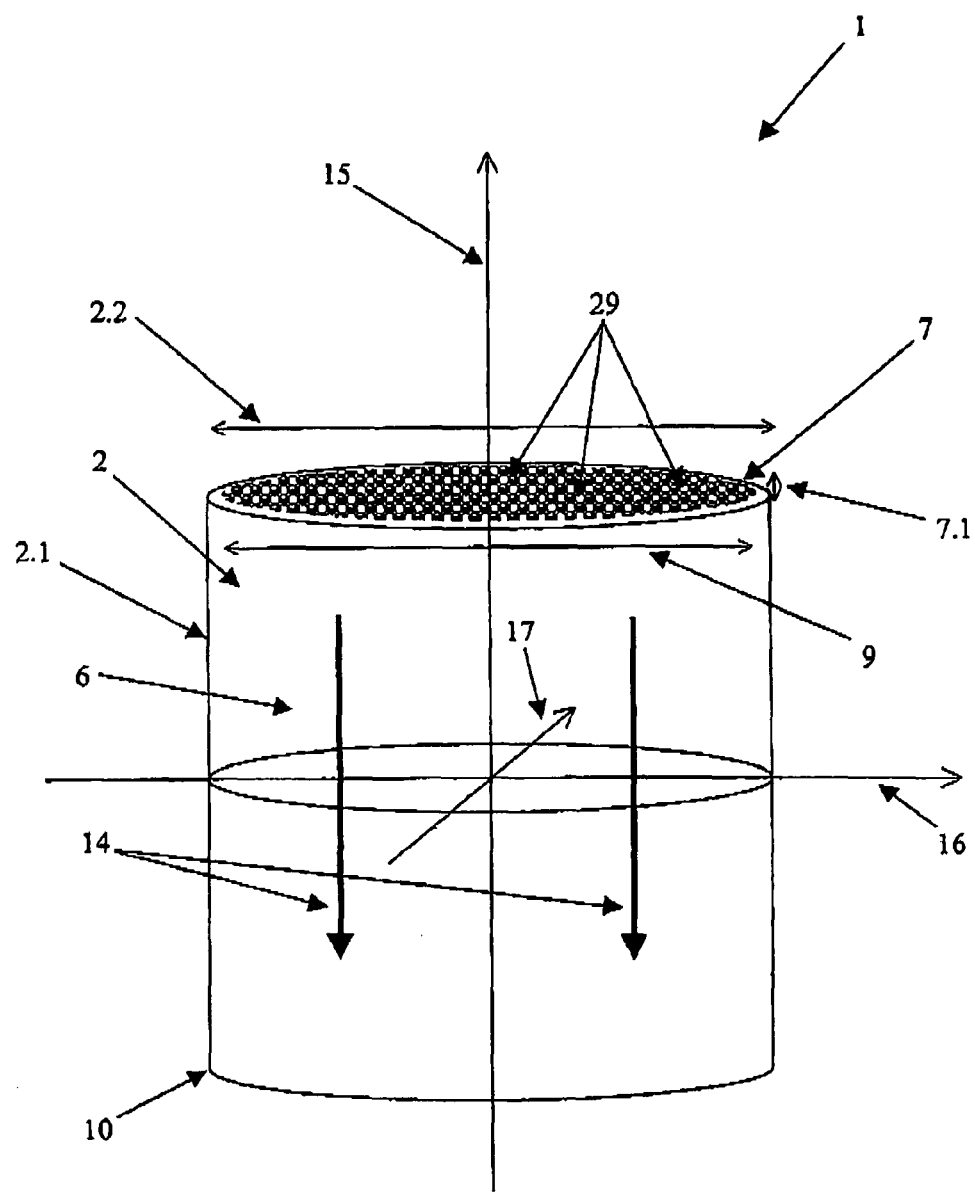

The fractionation of a substance mixture according to one or more physical or chemical parameters of the individual substances is generally highly regarded as an analytical method in chemistry and biotechnology. One fractionation technique consists of allowing the substance mixture (sample) to migrate through a suitable separation medium under the influence of physical or chemical parameters. In the process, the individual substances are fractionated according to their properties, due to interactions with the separation medium, and are subsequently present in the form of individual fractions. Examples of suitable parameters used are electric forces, pressure, centrifugal forces, gravity and osmotic forces, is diffusion, screen effects, extrusion, Vander-Waals forces, pH gradients. Depending on the application, the separation medium may be solid, liquid or colloidal. The different migration behavior of the individual fractions makes it generally possible to draw conclusions about their properties. In the case of a qualitative analysis of the substance mixture, only the relevant properties of the fractions during or after separation are measured and recorded and the fractions themselves are discarded. In the case of a quantitative analysis, the amounts of the individual fractions in the substance mixture are determined during or after separation. In the case of a preparative separation, the individual fractions are collected and are thus available for further processing or analysis.

The previously used techniques used are limited to the fractionation of the substance mixture in an essentially one-dimensional (referred to as 1D fractionation process hereinbelow) or two-dimensional (referred to as 2D fractionation process hereinbelow) separation medium:

In 1D fractionation processes, an individual sample is essentially placed in spot form at the opening of a (capillary) tube which contains the separation in medium and fractionated in the latter. The simultaneous fractionation of a plurality of samples requires a corresponding number of (capillary) tubes. Examples of this are capillary gel electrophoresis for DNA analysis and the high pressure liquid chromatography (HPLC) method.

In 2D fractionation processes, a plurality of individual samples are arranged adjacent to one another in a linear row (one-dimensionally). They pass through the essentially two-dimensional separation medium (in the form of a planar layer) in a plurality of parallel side-by-side migration tracks. The number of samples which can simultaneously be fractionated by this two-dimensional arrangement is determined by the number of tracks in the separation medium. Examples of this are polyacrylamide gel electrophoresis (PAGE) for DNA sequencing and 2D gel electrophoresis for protein analysis.

Due to geometry, the surface of the separation medium is large compared to its volume in 1D and 2D fractionation processes. Edge effects at the surfaces of the separation medium or at the boundary surfaces surrounding the separation medium therefore cause many disadvantages of the 1D and 2D fractionation processes. Examples of causes of these edge effects are interactions of the sample fractions or of the separation medium with the surrounding boundary surfaces and thermal effects.

The 1D fractionation process has, for example, the problem that capillary tubes used therefor, owing to their small diameter (usually a few ten mm), tend to be blocked by the samples adhering to the inside walls of the capillary tubes. The capillary is thereby rendered useless for further use. For the same reason, introducing the separation medium is not easy. Furthermore, bubbles which can form in this process or during separation can block the capillary.

A disadvantage of the 1D or 2D fractionation process, which likewise is based on edge effects, is the fact that widening of the bands can continue to arise owing to different migration times of the samples in the center of the separation medium compared to the edge regions ("smiling" effects). Enlargement of the band width, however, reduces the resolution of the analysis. This effect is caused by interactions between the samples and the surface which surrounds and receives the separation medium and, in the case of electrophoretic fractionation, by thermally caused inhomogeneities of the viscosity of the separation medium and by electroosmotic effects at its boundary surfaces.

Whereas in customary 1D fractionation processes a multiplicity of individual capillary tubes have to be filled individually, the separation medium, for example a gel, is introduced between two glass plates of a gel cassette in the case of some common 2D fractionation processes. In both cases, both the capillary tubes and the glass plates surrounding the separation medium must be extremely clean in order to minimize the edge effects mentioned above. Furthermore, there is a risk that bubbles are being formed during filling or during the separation process in the separation medium.

A common disadvantage of the two outlined fractionation processes is the fact that the number of simultaneously analyzed samples (maximally a few 100) is relatively small.

In order to solve or circumvent the problems listed above, a multiplicity of techniques have been proposed and methods worked out. The publications mentioned below circumscribe the prior art and demonstrate further aspects important for describing the proposed process.

U.S. Pat. No. 5,051,162 relates to a separating device based on the process of electrophoresis and combined with a fluorescence detector and to a sample container assigned to said detector. The electrophoretic device contains a number of gel layers in a plate-like shape which are essentially arranged parallel to one another, said plate-shaped (essentially two-dimensional) gel layers representing a multiplicity of migration lines along which sample fractions which have been labeled previously are able to migrate from top ends to bottom ends of the plate-shaped gel layers. An upper buffer container which contains a buffer solution in contact with the top ends of the plate-shaped gel layers is provided. Below said container there is another buffer container which likewise contains a buffer solution which is in connection with the bottom ends of the plate-shaped gel layers. There are devices for generating an electric potential between the buffer solution in said upper buffer container and the buffer solution contained in the lower container. This causes an electrophoretic force to act on the sample fractions and cause their migration along the migration lines. Excitation apparatus for fluorescence excitation of the appropriately labeled sample fractions are provided. The fractions migrate on said migration lines in the plate-shaped gel layers. Apparatus for individual and simultaneous detection of fluorescence light which is emitted by the sample fractions which are labeled and which move in said migration lines, the fluorescence light being emitted at the bottom ends of the plate-shaped gel layers, are provided.

The publication "Gene Expression Analysis by massively parallel signature sequencing (MPSS) on microbead arrays", Sidney Brenner, Maria Johnson, John Bridgham, George Golda, David H. Lloyd, Davida Johnson, Shujun Luo, Sarah McCurdy, Michael Foy, Mark Ewan et al. in Nature Biotechnology Vol. 18, June 2000, pages 630 to 634 describes a process for parallel analysis of a large number of sequences.

A system as published in this article comprises a flow cell which is mounted on a Peltier element and arranged below a confocal microscope. A filter and a CCD camera are arranged downstream of the con focal microscope, which camera is for its part connected to a computer. The flow of the sample material through a flow cell provided on the Peltier block is established via a reagent pump and a reservoir connected thereto and a valve block. This publication describes, inter alia, the arrangement of particles in a plane with the aid of a fluorescence-activated flow cytometer (FACS instrument) and is therefore relevant to the area of sample loading described in the present patent application.

From the publication "Effect of gelation conditions on the gel structure and resolving power of agarose-based DNA sequencing gels", Noriko Kusukawa, Mikhail V. Ostrovsky, Mark M. Garner, in Elektrophoresis 1999, Vol. 20, pages 1455 to 1460, the conditions under which agarose gels used for DNA sequencing gelatinize are studied. The gels used are subjected to both rapid cooling and gradual cooling. Analyses carried out by means of an electron microscope prove that the rapidly cooled gels have a homogeneous pore structure with a small average pore size compared to those gels which are cooled slowly and which have a substantially larger average pore size. Moreover, the rapidly cooled gels are optically more transparent. Photodetection of the sample is therefore easier.

In view of the solutions demonstrated in the prior art, the invention is based on the object of providing a process and a device both of which can be used to carry out a fractionation with high throughput rate of substance mixtures, for example mixtures of biomolecules, DNA fragments, proteins or the like and which make possible simultaneous (online) or subsequent detection and, additionally or alternatively, a qualitative, quantitative and preparative analysis.

According to the invention, this object is achieved by the features of claims 1 and 41.

Using the process proposed according to the invention and the device proposed for carrying out said process, it is possible to carry out a three-dimensional fractionation and thus an analysis of up to $10^4$ samples in parallel processing. In contrast to the above-described one- and two-dimensional separations, a three-dimensional fractionation is characterized by fractionation in a separation medium which extends essentially across three dimensions, further by delivering the samples to be fractionated to the separation medium in a two-dimensional arrangement. The process proposed according to the invention is distinguished in particular by a very simple operation with regard to delivering the sample mixtures to be analyzed. For this purpose, for example, DNA sequencing reactions may be carried out on a two-dimensional, i.e. essentially planar, support which is then transferred to the device in order to fractionate the individual samples. In gene expression analysis by "initial sequencing" of the expressed genes, the user may profit from all of the advantages of the SAGE process but can dispense with labor-intensive steps during sample preparation. Using the method of the invention of a 3-dimensional fractionation, individual samples may be analyzed with respect to three different and independent parameters. Parameters which may be mentioned here by way of example are the pH, the size and the hydrophobicity (or solubility) of the individual samples.

In the method proposed according to the invention of fractionation in a three-dimensional separation medium, the majority of the samples is not located at the edges of said medium so that the problems caused by edge effects in connection with fractionation processes carried out 1-dimensionally or 2-dimensionally, for example with respect to a widening of the bands (smiling effect), cannot occur. More specifically, the blocking of capillary tubes, which is inherent to the one-dimensional fractionation process, does not occur at all. The process proposed according to the invention provides, with respect to operation, the not inconsiderable advantage that it is now possible to dispense with filling individual capillary tubes, as is common in the 1-dimensional fractionation process. Furthermore, there are fewer demands to be made on the skills of the operators, compared to introducing the separation medium between two glass plates, as is required in some common two-dimensional fractionation processes, since, according to the process proposed according to the invention, the separation medium is poured into an essentially cylinder-shaped container. Moreover, there is, in the three-dimensional fractionation process, a substantially larger volume of separation medium available, in which the fractionation of a multiplicity of samples can be processed in parallel and simultaneously.

The forces required for causing the samples to migrate through the separation medium may be of a physical or chemical nature. Examples which may be listed here are electric forces, gravity, centrifugal forces or forces arising from diffusion, pressure and concentration gradients and from osmosis, which forces may act on the samples individually or in combination.

Electrophoresis

A preferred way of the three-dimensional separation process proposed according to the invention makes use of a force exerted on the samples by an electric field, in order to cause said samples to migrate through the separation medium. To this end, the samples are generally electrically charged; the separation process is referred to as electrophoresis. Owing to different charge and mass, the sample molecules move with different rates through the separation medium. Usually, the relative mobility of a substance, based on a co-fractionated standard, is indicated. This makes it possible not only to fractionate substances but also to characterize their migration behavior in more detail.

It is possible within the framework of the process proposed according to the invention and the device to utilize any known techniques for separation by the principle of electrophoresis. A distinction is made between electrophoretic separating methods in free solution (moving boundary electrophoresis, continuous support-free electrophoresis, capillary electrophoresis) and the fractionation in stabilizing media such as, for example, agarose gels or polyacrylamide gels.

The separation principle of electrophoresis is already a highly regarded analytical method in biotechnology, since the mechanism of separation is almost universally usable. Thus, for example, proteins, amino acids, peptides, blood plasma proteins, vitamins, enzymes, cells and cell components can be fractionated; moreover, it is a very gentle process, i.e., after the separation process, the samples are generally available for further preparative or analytical steps.

Joulean heat

One characteristic of electrophoresis is the current through the separation medium and, connected therewith, the conversion of electric energy into heat. This is referred to as Joulean heat; it is released within the medium penetrated by the electric current, in this case within the separation medium, and causes a temperature increase therein. The latter would cause, on the one hand, the samples to degrade and, on the other hand, the separating properties of the separation medium to be altered and, ultimately, said medium to degrade. Even before the separation medium is actually degraded, its electrical conductivity and viscosity are usually altered in a temperature-dependent manner. This is one of the main reasons for the abovementioned band-broadening effect (smiling effect) and for the migration tracks deviating from the desired (parallel) course. In all electrophoretic separating methods, therefore, care must be taken that the Joulean heat is removed from the separation medium in order to prevent an excessive increase in temperature in the latter. What matters, when thermostatting the separating structure, is not only the total heating power to be removed but also the generation or maintenance of a specific temperature profile within the separation medium. Depending on the separating process, maintaining a predefined temperature profile in the separation medium is more or less critical for the achievable resolution and the corresponding measures necessary for thermostatting are more or less complex.

Temperature Profile

By means of the proposed electrophoretic process of the invention and of the corresponding device, it is possible to keep the individual migration tracks of the samples through the separation medium, viewed in the radial direction, parallel to the vertical axis of the analytic hollow space by thermal insulation of the separation volume. For this purpose, a second space enclosing the first space may contain a medium which may serve as thermal insulation for the first space. Since ideally no heat is transported in the radial direction via the boundary wall of the first space into the surrounding space, the Joulean heat produced in the electrophoretic process can be removed exclusively via the end sides of a device suitable for carrying out the process proposed according to the invention. Under the idealizing assumptions that heat is only exchanged through heat conduction and, furthermore, that the heat is converted homogeneously in the separation medium, a temperature profile according to the following quadratic function:

$$T(z) = T_{max} - az^2$$

is obtained in the analytical hollow space. Due to the abovementioned, simplifying assumptions, the above formula is only a rough approximation, since in reality, other mechanisms of heat exchange (e.g. by irradiation) are present. Moreover, the Joulean heat conversion is not homogeneous, due inter alia to the inhomogeneous temperature along the z axis, which influences the electric field parameters via the electrolytical conductivity. In the inner central region of the first space and in its peripheral region, however, essentially the same temperature prevails, in other words, there is no temperature gradient in the radial (r) direction. The identical temperature profile along the vertical axis (z axis) inside the space and in its edge regions causes, viewed in the radial direction of the first space, an isotropic gel viscosity and ensures uniform ion mobility. The electric field lines produced in the first space and migration tracks of the samples from one electrode to the opposite electrode then run parallel to the z axis, i.e. the vertical axis, of the first space without diffraction in the radial direction.

According to the electrophoretic process proposed according to the invention, the temperature profile in the separation medium, parallel to its vertical axis (z axis), corresponds in the edge region of said medium to the temperature profile in the central region. This rules out a deflection, i.e. a bending, of the migration tracks owing to temperature influences. The formation of the migration tracks of the individual samples, which, starting from the sample application area, run strictly parallel to the Z axis, may be assisted by generating and maintaining in the first space and, where appropriate, in the second space surrounding the first one, a temperature profile by means of a temperature control device along the direction of sample migration at the particular surface, with the surface normal being perpendicular to the direction of sample migration, which temperature profile essentially corresponds to the temperature profile along the direction of sample migration in the center of the first space.

In order to maintain a temperature distribution which is essentially independent of a coordinate perpendicular to the direction of sample migration, the first space, and, where appropriate, the second space surrounding it, may be thermally insulated from a heat flow perpendicular to the direction of sample migration.

The electrically converted Joulean heat may also be removed by means of a temperature-control device in the first space, and, where appropriate in the second space surrounding the first one, at the respective end faces thereof—with a cylinder-shaped design, with the surface normal being the same as or opposite the direction of sample migration.

According to the electrophoretic process proposed according to the invention, electrode elements which may be configured, for example, in a plate- or ring-shaped manner are assigned to the separating structure in such a way that, when applying an electric voltage to said elements, the (electrically charged) individual samples essentially migrate in the direction of the vertical axis of the separation device.

The second space may be surrounded by a further space or may be connected thereto, in which further space a solvent such as, for example, an electrolyte or a buffer medium is present which is in contact with the end sides of the essentially cylindrically arranged separating structure. Setting or maintaining desired electrical, chemical or physical properties of the separation medium and of the solvent surrounding the electrodes may be promoted by circulating the solvent present in the further space, be it an electrolyte or a buffer medium, between the electrode elements. A circulation may advantageously be connected to removing heat via the end faces of the first space, and, where appropriate, of the second space. The buffer medium is advantageously circulated in the radial diction, either from the center into the peripheral region or vice versa, and this process may be carried out by means of a circulating apparatus (pump). The, for example electrical, properties, or else other physical and chemical properties, of the solvent advantageously correspond to those of the separation medium received in the first space. The further space may be connected to an external reservoir in order to improve an ion exchange.

In the case of electrophoretic fractionation, the separation medium used in the process proposed according to the invention is received within the first space in such a way that a ratio of its radial extension to its longitudinal expansion of >0.2, preferably >0.3, particularly preferably greater than >0.5, is obtained.

Depending on the application, the separation medium may be solid, liquid or colloidal; it may also be a transparent or a nontransparent separation medium. Examples of separation media which may be mentioned, are polyacrylamide, agarose or else hydroxyl cellulose.

Depending on the separation medium used, the preferred buffer medium used is a medium whose physical, electrical and chemical properties are as close as possible to those of the selected separation medium.

Sample Application

The samples may be applied by introducing a two-dimensional layer (sample plate) in or on which the individual samples are two-dimensionally arranged in an essentially planar manner. Such a sample plate for receiving samples may be integrated into the separation layer itself. The individual samples may be locally fixed in or on a support material or on essentially 2-dimensional arrangements of point-like elevations or depressions, for example applied by arrays of pins, microelectrodes, hollow bodies, pipettes, tips. The sample plates used preferably comprise a porous support material. The individual samples of the particular sample application may, for example, also be localizable on the sample plate by means of electric or magnetic forces. Likewise, the samples may also be applied directly to the separation medium, for example in regularly arranged depressions located at one of its interfaces. In this case, a part of the separation medium itself is the sample plate. However, sample plates are usually separate devices for handling the samples.

The individual samples may be subjected to chemical reactions or physical treatments or measurements prior to the separation process. This takes place preferably in or on the sample plate, or in a device from which the individual samples can be transferred to the sample plate. The individual samples may be amplified, for example, from individual molecules or from a multiplicity of molecules of the same kind, it being possible to use for this purpose, for example, in addition to the PCR method, also cloning and a subsequent selective propagation. In the same way, it is also possible to carry out reactions preceding the separation (e.g. DNA sequencing reactions).

A two-dimensional distribution of the individual samples on the sample plate or on a device from which the individual samples can be transferred to the sample plates may be carried out, for example, using a cell sorter or a fluorescence-activated cell sorter (FACS). For this purpose, for example, the individual samples may be located on or in particles, preferably in host organisms, for example yeasts, bacteria or "competent cells". In this context, the particles are distributed owing to the physical or chemical properties measured in each case. Said physical properties may be, for example, the intensity or the wavelength of emitted fluorescence light. The two-dimensional distribution of the individual samples on the sample plate is carried out in such a way that the distance between neighboring individual samples does not fall short of a minimum distance. Said minimum distance is essentially dependent on the type of separation and on the samples and must be chosen so as to ensure the independent separation and detection of the individual samples. The distribution of particles, for example competent cells, may be followed by amplification steps. In this connection, the sorting and distributing of organisms carrying a DNA section (insert) to be sequenced are of high practical importance. In the case of conventional sequencing techniques, the presence of such a DNA section (insert) is concluded from a color change of the organism. For this purpose, the organism is made to form a dye by way of targeted manipulation of its DNA. In organisms carrying an insert the latter interferes with said dye formation. Manipulation of the DNA of said organism may be modified in such a way that the dye formed, for example GFP (=Green Fluorescent Protein), or the color change, may be recorded by a florescence-activated cell sorter (FACS instrument) and may thus contribute as a criterion to the automatic sorting and distribution of organisms on the sample plate. The sample distribution by means of measured properties may be followed by further chemical reactions or physical treatment steps, for example sequencing reactions, preferably in the sample plate.

Separation According to 3 Parameters

The individual samples of the particular sample application may be prepared in such a way that first a plurality of samples are fractionated according to one parameter by parallel processing in an essentially two-dimensional separation medium. The two-dimensional separating medium containing the fractionated sample fractions is then contacted, as a sample plate, with an interface of the three-dimensional separation medium. The samples contained in the two-dimensional separation medium may then be fractionated according to a further parameter in the three-dimensional separation medium by migrating in a direction which is oriented essentially perpendicularly toward their original direction of movement. The fractionation through the two-dimensional separation medium may moreover be preceded by a preseparation in a one-dimensional separation medium, so that it is possible, using the process proposed according to the invention, to fractionate samples according to a total of three independent parameters. Alternatively, it is possible to contact, instead of the two-dimensional separation medium, a plurality of one-dimensional separation media containing preseparated sample fractions in an essentially parallel arrangement as the sample plate with the interface of the three-dimensional separation medium and to fractionate said samples in the latter. In this way, the process proposed according to the invention enables samples to be fractionated according to only two parameters but by way of parallel processing with high throughput. The samples may be detected by appropriate methods in each case between the individual separation steps and, additionally or alternatively, the separation medium and/or the samples may be treated chemically or physically. It is also possible, where appropriate, to remove individual sample fractions from the separation medium for further analytical or preparative steps.

It is possible to utilize for the one- or two-dimensional preseparation of the individual samples, for example, the above-described electrophoretic techniques using the above-described sample plates, which contain a suitable separation medium for this purpose. This is particularly important for the proposed application of fractionating protein mixtures according to three independent parameters (e.g. pH, size, hydrophobicity or solubility) by means of the three-dimensional separation process proposed according to the invention.

Detection, Fraction Collector

Samples may be detected and analyzed qualitatively and quantitatively by a multiplicity of various techniques within the framework of the three-dimensional separation process proposed according to the invention. Preference is given to using photodetection processes.

In the simplest case, detection is carried out by simple viewing.

In many cases, it is sensible to combine detection and preparative collection of the sample fractions. In exceptional cases, the individual sample fractions are only collected preparatively, with a detection being dispensed with.

It is possible to distinguish two methods of collecting the sample fractions.

The first implementation variant collects the sample fractions immediately at an interface of the separation medium and stores them there in or on a suitable collecting medium. The collecting medium preferably comprises a membrane or individual sample plates which may be moved past an interface of the separation medium at regular time intervals. A regular transport of the collecting membrane from the separating device or a regular exchange of the sample plates then deposits the sample fractions on various subareas of the membrane or on various sample plates, depending on the retention time.

In the second variant, the samples are directed through an array of capillaries, tubes or tubing out of the separating device and collected by an external fraction collector.

The detection may take place during sample migration (online detection) or after the separation has finished. Detection of the samples during their migration may be directed back to a two-dimensional imaging process. For this purpose, the sample fractions are detected when passing through a selected, two-dimensional planar detection region. The detection region which is oriented essentially perpendicularly to the direction of sample migration is located preferably close to an interface of the separation medium and may be inside or outside said separation medium. This essentially two-dimensional detection region may receive in time intervals, for example by means of the detection apparatus described below, a continuous series of two-dimensional images and record them in a suitable manner. The spatial distances along the direction of migration between the sample fractions, which result from their separation, are thus converted into time intervals of their passage through the detection region.

A detection after the end of the separation process requires a three-dimensional imaging process. To this end, a stereoscopic imaging process may be used, for example. As an alternative to this, an essentially two-dimensionally defined detection region may be moved through the separation medium, preferably in the direction of the vertical axis (z axis) thereof (scanning). This detection region may receive, for example by means of the detection apparatus described below, a series of two-dimensional images and record them in a suitable manner.

However, by cutting the three-dimensional separation medium into disks, for example by parallel sections, after the separation process has finished, it is possible, even in the case of detection after the separation process has finished, to go back to a conventional two-dimensional imaging process. The sections preferably run parallel or perpendicularly to the direction of sample migration. The essentially two-dimensional disks of the separation medium obtained in this way may be depicted by customary, suitable 2D scanning methods. Individual sample fractions may then also be readily isolated preparatively by removing them from the disks.

Confocal Detection

A preferred technique for online detection is a confocal detection apparatus whose measuring head may be designed as a multiple measuring head. The confocal detection apparatus is provided with one or more optical systems which are arranged so as for the object-side point or line foci of the illumination beam paths to coincide with those of the detection beam paths. One and the same or different optical systems may serve to focus the illumination light and record the light emitting from the samples in the detection region. In the latter case, the beam paths of the optical systems for illumination and detection are preferably arranged rectangularly to one another. Moreover, in this case, the dichroic beam splitter for separating the beam paths of illumination and detection apparatus may be dispensed with.

Choosing a confocal detection arrangement may reduce background radiation caused by (Rayleigh) scattering in the separation medium and in the surrounding medium and achieve a better spatial resolution in the direction of the optical axis. Relatively large areas of the cross-sectional area of the first space can be scanned simultaneously by means of a multiple measuring head. In order to detect individual samples labeled with fluorescent dyes, the (multiple) measuring head of the confocal detection apparatus may be provided with optical absorption filters and, alternatively or additionally, with interference filters.

The image may be built by moving the detection apparatus in the x, y; r, $\omega$ direction with respect to a cross-sectional area of the first space which contains the separation medium and the individual samples to be fractionated therein (scanning). The usually electrical signal produced in the detection apparatus during scanning may then be delivered to suitable apparatus for amplification and recording.

Spot-Confocal Detection

According to a further possible implementation variant of confocal detection, the detection region may be illuminated in a spot-like fashion. In a preferred embodiment, one (or more) monochromatic, coherent light sources (e.g. laser) is used. The beam(s) may be deflected by means of a dichroic beam splitter toward a lens which focuses it/them on a point in the plane of detection. In the process, the beam(s) may, to give an example, hit fluorescent molecules which, due to excitation with light of the laser wavelength, emit fluorescence light of a different, longer wavelength. The same or a different lens records, depending on the numerical aperture, part of the emitted light which is redirected by the dichroic beam splitter to a detector, for example a photomultiplier, avalanche diode or a CCD camera. Depending on the strength of the light signal, a corresponding detector signal is generated. The optical beam paths of the illumination apparatus and the detection apparatus are designed such that their two object-side focal points are superimposed in the detection region in a (spot-) confocal manner. An image can be constructed by moving (scanning) the measuring head in the x,y or $\Omega$,r direction with respect to the separation medium.

Cylindrical-Confocal Detection

A simplified detection apparatus makes use of a cylindrical-confocal arrangement of an illumination device in combination with a line detector. The radiation emitting from the illumination line is linearly focused into the detection region by a suitable optical system. The illuminated line in the detection region is projected onto the detection line by a suitable optical system. Cylindrical-confocal refers to the arrangement of the optical systems assigned to the line detector and to the illumination device, when the two object-side focal lines of the assigned optical beam paths are congruently superimposed.

The detection region may be illuminated, for example, by means of a line-shaped arrangement of light-emitting diodes or laser diodes or by means of a laser beam which is moved in a fan-like manner or has been widened accordingly. The signal-to-noise ratio may be improved in accordance with the mode-locking process by addressing the individual light-emitting diodes or laser diodes or by moving the laser beam synchronized with the read-out process of the line detector. The optical system which is assigned to a cylindrical-confocal combination of illumination apparatus and detection apparatus may contain one or more gradient index lens fields, cylinder lenses, microlens fields or a combination of these optical elements.

Gradient Index Lenses

Preference is given to using one or more gradient index lens fields. Such a lens field (array) comprises a multiplicity of individual gradient index lenses arranged close together. Gradient index lenses are characterized by a continuous decrease in the refractive index within the cylinder-shaped lens body from the central axis outward. Light beams entering on the end sides are thereby deflected sinusoidally within the lens. Gradient index lenses are manufactured with diameters of from about 0.1 to 2 millimeters. The length of the cylinder-shaped lens body determines the focal length and the optical imaging properties of the lens. Gradient index lenses of a particular length generate a vertical 1-to-1 image. When a plurality of such lenses are arranged to give an array, the images of individual lenses superimpose to give a spatially continuous, vertical 1-to-1 image of any size. Projecting the light of a light-emitting diode line, or preferably a laser diode line, by means of a gradient index lens array into the detection region may illuminate in the latter a line-shaped region in a spatially selective manner. The same lens array may serve to project in a spatially selective manner the illuminated region within the separation medium onto a line-shaped detection apparatus, for example a CCD line or photodiode line. In this case, the light emitting from the illuminated region in the detection region may be separated wavelength-specifically from the light emitting from the illumination apparatus by means of a dichroic beam splitter and delivered to the detection apparatus. In addition to the dichroic beam splitter, other optical absorption and interference filters may be used in order to improve the spectral selectivity of the detection.

Orthogonal Cylindrical-Confocal Detection

Another implementation variant of the detection apparatus makes use of an orthogonal cylindrical-confocal arrangement of a line-shaped illumination device in combination with a line detector. For this purpose, it is possible, by projecting the light of a light-emitting diode line, or preferably a laser diode line, by means of a suitable optical system, preferably by means of a cylinder lens, into the detection region, to illuminate in the latter a line-shaped region in a spacially selective manner. The illuminated region may be projected onto the detection apparatus by means of one or two gradient index lens array(s) having an optical axis arranged at an angle to the optical axis of the illumination apparatus. The essentially rectangular (orthogonal-confocal) arrangement of the optical axes of illumination and detection apparatus may reduce the background radiation caused by (Rayleigh) scattering of the illumination light in the separation medium and achieve a better spatial resolution in the direction of the z axis. Moreover, in this case, the dichroic beam splitter for separating the beam paths of illumination and detection apparatus may be dispensed with. In this embodiment of the optical system, too, optical absorption and interference filters may be used in order to improve the spectral selectivity of detection. The above-described variants of cylindrical-confocal arrangements may also be designed as a multiple measuring head by combining several of those illumination and detection lines. The illumination and detection units combined in such a multiple measuring head may also be designed individually for receiving different radiation, for example one with different wavelength or polarization.

An image is constructed by shifting the above-described illumination and detection lines having optical axes arranged essentially orthogonally to one another and confocally superimposed focal lines one-dimensionally in the x or ω direction with respect to the separation medium (scanning).

Detector Integration in Electrode

In the case of electrophoretic separation, a spot-confocal or cylindrical-confocal detection apparatus may be integrated in one of the electrodes, preferably the electrode to which the samples migrate within the separation medium of the first space. The scanning process then moves the electrode together with the detector. This prevents the detection apparatus from impairing the homogeneity of the electric field built up in the separation medium, averaged over one or more scanning periods. The arrangement of a confocal detection apparatus above the separation medium prevents gas bubbles produced in the course of the electrophoretic process above the first space from impairing projection of the fluorescence light onto the detector.

Illumination Perpendicular to the Direction of Migration

In a further implementation variant of a detection apparatus, an illumination apparatus may be arranged so as for its optical axis to be essentially perpendicular to the direction of sample migration. According to this arrangement, a preferably monochromatic, coherent source of radiation, for example one or more lasers, illuminates an essentially two-dimensionally extending detection region oriented essentially perpendicularly to the direction of sample migration. For this purpose, the light beam(s) may be deflected in a fan-like manner or divided by a suitable optical system, for example by galvanometric deflection apparatus, rotating polygonal mirrors or cylinder lenses.

In this connection, the detection region may be located within the separation medium or outside the separation medium, preferably close to one its interfaces. In the case of detection during sample migration (online detection), the detection region remains stationary with respect to the separation medium. The sample fractions are then detected when passing through the detection region. In the case of detection after migration has finished, the detection region may be shifted through the separation medium, preferably in the direction of its vertical axis (z axis), in order to record the image (scanning). For this purpose, the separation medium may be removed from the separating device and transferred to a separate detection device.

Preference is given to choosing the direction of polarization of the illumination light in such a way that only a minimal fraction of the background radiation caused by (Rayleigh) scattering in the separation medium and the surrounding solvent is emitted in the direction of the detection apparatus. Preference is given to choosing the wavelength of the illumination light so as to achieve optimal fluorescence excitation of the appropriately labeled sample fractions and to minimize the interfering radiation which emits from the separation medium and the surrounding solvent and which is caused by intrinsic fluorescence. Preference is given to using monochromatic radiation sources with a high degree of polarization, for example lasers.

The radiation emitted by the sample fractions may be received by a detection apparatus whose optical axis is essentially parallel to the vertical axis of the cylinder-shaped separation body and intersects one of the latter's end faces. Said detection apparatus then captures radiation which emits at the end face from the separation body. In this connection, the optical axis of the detection apparatus may be oriented in the direction opposite to migration, but preferably in the direction of sample migration.

However, in the case of relatively longitudinal separation bodies, i.e. those having a ratio of their radial to their longitudinal extension of <1, for example, it may also be advantageous for the detection apparatus to be arranged with its optical axis being essentially tilted toward the vertical axis of the separation body. In this case, the optical axis of the detection system intersects the wall surface of the essentially cylinder-shaped separation body and may be oriented in the direction of or opposite to migration. The detection apparatus then captures radiation which, starting from the detection region, emits through the wall surface which completely surrounds the separation body, for example via an appropriate window.

In any case, care must be taken that an optical system with high numerical aperture is used in the detection apparatus. The radiation from the plane of detection, or from a subregion of said plane of detection, is projected two-dimensionally by the optical system, for example, to a high-resolution CCD camera which is downstream of the detection apparatus. If only a subregion of the plane of detection is projected, then the detection apparatus, in order to cover the entire detection region, may be shifted with respect to the latter accordingly in the x, y, or ω direction (scanning).

A device used for carrying out the process of the invention comprises a separation structure containing at least one space which extends essentially across three space coordinates and which has been constructed so as to be able to filled with a separation medium. The samples to be fractionated are delivered to the separation medium at one end face. A detection apparatus is assigned to the separation arrangement formed in this way. As an alternative or in addition to the detection apparatus, a device for preparatively collecting the individual sample fractions (fraction collector) may be assigned. In order to induce the samples to migrate through the separation medium, the separating device is advantageously designed in such a way that it is possible to build up therein an electric field or that it can be subjected to centrifugal accelerations or that a hydrostatic pressure or gas pressure can be applied using a suitable device, for example by a pump or a pneumatic system.

Electrophoretic Device

In the case of using the device for electrophoresis, the arrangement should comprise a second space which surrounds the first space, is arranged concentrically thereto and has a heat insulation. The first space should have a radius-to-length ratio R/Z of greater than 0.5 in order to ensure good removal of the Joulean heat released during electrophoresis through the end sides of the separation medium contained in said space. The heat is removed particularly well if the radius-to-length ratio R/Z is greater than 1. Moreover, the total number of the individual samples which can be fractionated using the device increases with the square of the radius of the first space containing the separation medium. In a preferred embodiment of the electrophoretic separating structure proposed according to the invention, the second space surrounding the first space may contain an insulating medium which serves to thermally insulate the separation body in the radial direction. The insulation effects the formation of a temperature profile in the first space, which is substantially independent of the radial (r) coordinate. The formation of a radial (r) coordinate-independent temperature profile in the first space may be assisted by controlling the temperature of the space boundary of the first space along the direction of sample migration (vertical axis or z axis). The temperature of the space boundary may be controlled, for example, electrically or by means of a temperature-control medium.

In a preferred embodiment of the separating structure, the end faces of the first space and, where appropriate, of the second space are covered by electrodes in such a way that, when applying an electric voltage, an electric field as homogeneous as possible is produced in the separation medium received by the first space. The electrode elements preferably have a plate-like shape and contain electrically conducting compounds which are arranged in each case on the side of said electrodes, which face away from the separation medium. The spaces surrounding the electrodes are adjacent to the separation medium. They are designed so as to be able to be filled with a liquid or an electrolyte, preferably a buffer medium, and, furthermore, so as to enable a heat flow via the end faces of the separation medium. Preference is given to providing a heat exchange device there which is advantageously combined with a temperature-control device. Preference is given to using the liquid surrounding the electrodes as the heat exchange medium.

If in the device proposed according to the invention for carrying out the process the second space harboring the heat insulation is enclosed by a reservoir which is connected with the spaces surrounding the electrodes in a manner which makes an exchange possible, then it is possible, in the case of the application to electrophoresis, to achieve a diffusive ion exchange between the liquid volumes located at the anode-side and cathode-side end regions of the first space. This makes it possible, on the one hand, to reduce the amount of the buffer medium required and, on the other hand, to assist setting or keeping constant desired chemical, physical and electrical properties of said buffer medium. In a preferred embodiment, the buffer medium is actively exchanged using a suitable circulating equipment, for example a pump. In a particularly advantageous embodiment, thermostatting, for example using a heat exchanger, by means of which the Joulean heat emitting at the end faces of the separation medium can be removed, may be provided in the circulation circuit.

Detection Device

Photodetection devices may be classified according to the type of data receiving. The following devices may be distinguished:
a) the 3D image-taking system for detecting the sample fractions after the separation process has finished or
b) the online detection system for detecting the sample fractions during the separation process.

The 3D image-taking system is designed in such a way that, during image-taking, at least one photometric reading can be assigned to each volume element of the separation medium, i.e. each data set comprises a position vector with 3 coordinates, to which at least one photometric reading is assigned.

The online detection system is designed in such a way that a two-dimensional position vector and additionally the time as a third coordinate are assigned to each photometric reading. Online detection systems are designed so as to record readings from a stationary plane (plane of detection) through which the sample fractions migrate at regular time intervals. For this purpose, the plane of detection may be within the separation medium or outside the separation medium close to an interface thereof.

For online detection, again two types of devices may be distinguished:
a) confocal scanners and
b) 2D image-taking systems with orthogonal illumination device.

Confocal Scanners

Suitable advantageous implementation variants of confocal scanners are spot-confocal or cylindrical-confocal scanners having a simple measuring head or a multiple measuring head. Scanners with multiple measuring head have the advantage of requiring shorter read-out times for reading out a given area and of the scanning process being able to carried out at lower rates. Moreover, the individual measuring heads which are combined to give a multiple measuring head can be set individually for measuring radiation with different properties, for example different wavelength. Incorporation of the measuring head into one of the electrodes is particularly advantageous when operating confocal scanners in connection with electrophoretic separating devices.

Cylindrical-Confocal Scanners

A particularly simple and, at the same time, advantageous scanner is characterized by cylindrical-confocal optics. Such a scanner is characterized by cylindrical illumination optics and by one or more preferably coherent radiation sources, for example lasers with optics for beam expansion. The illumination optics are designed so as to focus the radiation of the radiation sources into the plane of detection. Choosing cylinder optics, preferably a cylinder lens, results in an illuminated focal line in the plane of detection.

The detection optics are set in such a way that said line is projected onto a line detector. The optical axes of illumination optics and detection optics are advantageously oriented at an angle to one another. A structure using two illumination apparatus which are arranged essentially symmetrically on both sides of the detection optics is also advantageous. The detection optics are characterized by true-point imaging properties. Preference is given to using arrays of lenses. The use of a gradient index lens array is particularly advantageous.

Optics and line detector mechanically form a unit which is mounted on a movable carriage. Using a drive device, the carriage may be moved along a Cartesian coordinate or rotate around one axis. The control and read-out electronics for the line detector are synchronized to the movement of the carriage. A data recorder and a computer system device for data evaluation are assigned to the scanning device constructed in this way.

Spot-Confocal Scanner

Compared to cylindrical-confocal scanners, spot-confocal scanners have a superior local resolution. The local resolution in the direction of the optical axis (depth of field) is particularly important here. However, electronic control, data recording and data evaluation are more complicated for spot-confocal scanners and it has to be taken into account that the above-described mechanical carriage must be modified in such a way that the spot-confocal measuring head can carry out movements along two coordinates and thus can scan an area (plane of detection).

Orthogonal Illumination 2D image-taking systems having an orthogonal illumination device for a plane of detection are characterized by the following features:

They have an illumination apparatus formed by a preferably coherent light source, for example one or more lasers with beam expansion optics, which is attached to the separating device in such a way that a plane of detection is spanned in the separation medium or close to an interface of said separation medium in such a way that the sample fragments can migrate through this plane. A detection system consisting of a lens and a detector, preferably a CCD camera, is assigned to the illumination device. The lens and the detector are arranged so as for the detection region to be projected two-dimensionally onto the detector. The properties of the lens are chosen in such a way that the projection takes place with a high aperture and, at the same time, a high local resolution. The optical axis of the lens may run essentially parallel to the direction of sample migration. In this arrangement, the lens receives radiation which is emitted at the end sides of the separation medium.

However, the optical axis of the lens may also be tilted with respect to the direction of migration. In this case, the detection device is provided at the side of the separating device. In this case it is recommended to provide for a prism-shaped window toward the separation space, whose optical properties, in particular the refractive index, are similar to those of the separation medium. It may be advantageous in such a structure to arrange in the detection region tilted with respect to the direction of sample migration, preferably perpendicularly to the optical axis of the lens. The advantage of this is better imaging properties, but the disadvantage is that differences in the sample run times due to different paths through the separation medium must be corrected.

The data may be recorded by a suitable recorder which receives data sets, essentially in the form of two-dimensional images, at periodic intervals.

By adapting to the above-described 2D image-taking system a translation mechanism which shifts the detection region along an axis, preferably the vertical axis, through the separation medium, it is possible to construct a 3D image-taking device for detecting sample fractions after their separation has finished. In this case, the data receiving device is synchronized to the translation device. The above-described 3D image-taking device may also be constructed independently of the separating device. In this case, the separation medium may be removed from the separating device after the separation process has finished and be transferred to the separate 3D image recording device.

Preparative Collection of Individual Fractions

A fraction collecting device may be provided alternatively or, preferably, additionally to the sample detection apparatus. It is particularly advantageous to couple said fraction collecting device to said sample detection apparatus. Such a coupling enables data to be exchanged and assigned and makes possible a one-sided or reciprocal control between the two units.

Two implementation variants may be distinguished:

The first implementation variant is characterized by a transport mechanism for collecting media such as plates, membranes, microtiter plates or arrays of reagent tubes. The collecting medium preferably consists of a membrane or of individual sample plates. The transport mechanism places the collecting media immediately at an interface of the separation medium, replaces them at regular time intervals and transports them out of the separating device. Preference is given to utilizing an unwinding device, similar to a film projector, which transports a membrane. The properties of said membrane are chosen in such a way that the fractions eluting from the separation medium are bound to said membrane. The regular transport of the collecting membrane from the separating device, or a regular replacing of the sample plates, deposits the sample fractions, depending on the retention time, on different subareas of the membrane, or on different sample plates. The second implementation variant is characterized by a capillary array or an array of hollow bodies such as, for example, tubes or tubing. In each case, one end is positioned as the inlet close to the sample exiting area at the interface of the separation medium. The outlets are located outside the separating device above a fraction collecting device, preferably a collecting device for microtiter plates or sample plates. Transport from the inlet is effected by a pneumatic system which acts jointly on all capillaries or individually on each capillary or by electric forces. The electric field or pneumatic system are designed in such a way that the sample fractions are transported out of the separating apparatus and transferred to the fraction collecting device.

A mold device is provided for processing and preparing sample plates and for processing the surface of separation bodies. The mold is a plate-shaped tool whose surface has elevations or depressions in a preferably periodic two-dimensional arrangement. The surface material is preferably chosen so as, on the one hand, to promote, or at least not to hinder, molding processes such as, for example, polymerization of acrylamide, for example, and, on the other hand, to have good separating properties, i.e. that there is only low, or no, affinity to the materials to be formed.

Sample Plates

Sample plates are primarily assigned to the above-described three-dimensional separating process of the invention and to the separating device. However, their properties and possible uses are designed in such a way that their application may also be extended further. Thus they are generally useful items of practical use in the field of cloning, as described.

An essential function of sample plates within the framework of the three-dimensional separation process proposed according to the invention is the loading of the separating device. For this purpose, sample plates preferably used within the framework of the three-dimensional separation have to be adapted in several aspects to the separating device described and to the specific applications.

One of the main features of sample plates used within the framework of three-dimensional separation is that their format and dimensions are adapted essentially to those of the separating device. Since the separating device is constructed preferably cylindrically, a circular format is one of the possible advantageous formats. However, such a format is difficult to operate in customary automatic laboratory operating systems, since these are usually adapted to rectangular formats. Therefore, as a compromise, a quadratic format seems advantageous. The dimensions of the sample plates are chosen in such a way that they can be arranged close to an (end-side) interface of the separation medium.

In order to load the separating device, the sample plate containing the individual samples is preferably arranged close to an (end-side) interface of the separation medium. The individual samples are transferred from the sample plate to the separation medium by means of suitable physical or chemical parameters such as, for example, electric forces, pressure, centrifugal forces, gravity, osmotic forces, diffusion or capillary forces. Sample plates are therefore preferably fabricated, at least partially, from porous material. The porous or permeable material enables electric currents, liquid flows, gas streams, a diffusive exchange of material, etc. In this context, it is advantageous if the porous material is arranged so as to enable a transport of material in the direction of or opposite to the surface normal. With respect to its material properties such as, for example, pore size and absorbency, the porous material of the sample plates may preferably be such that it enables samples to be locally fixed on or embedded in said material.

Samples may also be locally fixed by the sample plates having solid separating walls, for example in the shape of a honeycomb structure or depressions in the surface. A local fixing may likewise be made possible via electrostatic forces by means of electrodes or via magnetic fixing to small particles of magnetic material. For this purpose, the electrodes or particles may be arranged on the surface of the sample plates or may be set therein.

Preference is also given to choosing for sample plates those materials which resist relatively high thermal stress, in particular thermal stress as it occurs in the PCR process. It is at least advantageous if at least the components of the sample plate which are involved in locally fixing the samples resist relatively high temperatures.

Sample plates advantageously also consist of materials which do not impair the growth of cells or which may selectively or else nonselectively favor the growth of cells. This is particularly important for those types of sample plates which are intended to be used for the FACS-assisted cloning process described in the present patent application.

Not all of the specifications illustrated as advantageous can be combined in one embodiment of sample plates. Therefore, it is advantageous to provide sample plates for very specific applications. Examples of this are sample plates for cell culture using nutrient media, for example agarose, sample plates for the PCR process, sample plates for silica filtration, sample plates for separation purposes, which contain a suitable separation medium, for example agarose or polyacrylamide, or special sample plates for chemical, physical or photometric measurement purposes.

Sample Transport/Exchange

Substances such as, for example, samples or reagents may be removed from or delivered to sample plates or the loading layer of a separation body by using suitable loading tools. Due to the large number of samples (in the order of magnitude of 10 000 individual samples), such a tool is characterized by a regular arrangement (array) of hollow bodies, tips, pins or capillaries which are capable of simultaneously receiving and transferring a multiplicity of samples.

Advantageously, this array is characterized by the individual elements of said array having connections. Said connections are preferably pneumatic connections or electrical contacts or a combination thereof. The elements are designed in such a way that they can receive or give off or assist in receiving or giving off substances.

Another tool for filling sample plates consists of a translation mechanism for sample plates. Said translation mechanism is controlled by a cell sorter, preferably an FACS instrument. The controller (cell sorter, FACS instrument), by way of its structure and its control program, is designed in such a way that droplets or parts of a liquid flow are deflected, for example by a diaphragm, in the direction of the sample plate. Addressing the mechanical translation device in order to move the sample plate in one or more coordinates is likewise carried out by the controller.

The process proposed according to the invention and the device provided therefor are particularly suitable instruments for fractionating, to be carried out simultaneously, a very large number of mixtures of biomolecules or chemical substances such as, for example, DNA fragments, proteins, blood or blood plasma in a three-dimensional separation medium. They can be used for any analytical techniques which require only a relatively low separating accuracy and in which the exact identity of the individual samples is not crucially important. The preferred main application of the process proposed according to the invention is in the field of three-dimensional electrophoresis. It is possible, by means of the process proposed according to the invention, to fractionate simultaneously and with parallel processing several thousand individual samples containing a multiplicity of short DNA sections (some 10 to 100 bases). This provides the use of the process proposed according to the invention for gene expression analysis according to the SAGE technique (serial analysis of gene expression), with, however, the complicated step of linking the individual DNA sections, which is required in this technique, being avoided.

If relatively long sequences of the individual clones (150 to 200 bp (base pairs)) are required, the process proposed according to the invention and the separating structures suitable therefor may be used for shotgun sequencing. Another field of application of the process proposed according to the invention would be the DNA fingerprint technique.

Finally, further fields of application of the process proposed according to the invention are protein analysis and expression analysis of biomolecules. Here, protein mixtures and the like can be fractionated, in particular, with respect to three parameters which may be, for example, the pH, the size and the hydrophobicity (or solubility) of said biomolecules. Further applications are the fractionation of substances, inorganic or organic molecules, DNA, RNA, lipids, peptides, amino acids, the sequence analysis of nucleic acids, detection of point mutations, the use of the separation medium 6 in expression analysis and protein analysis with respect to a plurality of parameters such as, for example, pH, size and hydrophobicity (or solubility) of the individual samples 29, the diagnosis of diseases and the analysis of metabolic products.

DRAWINGS

Figure 2:
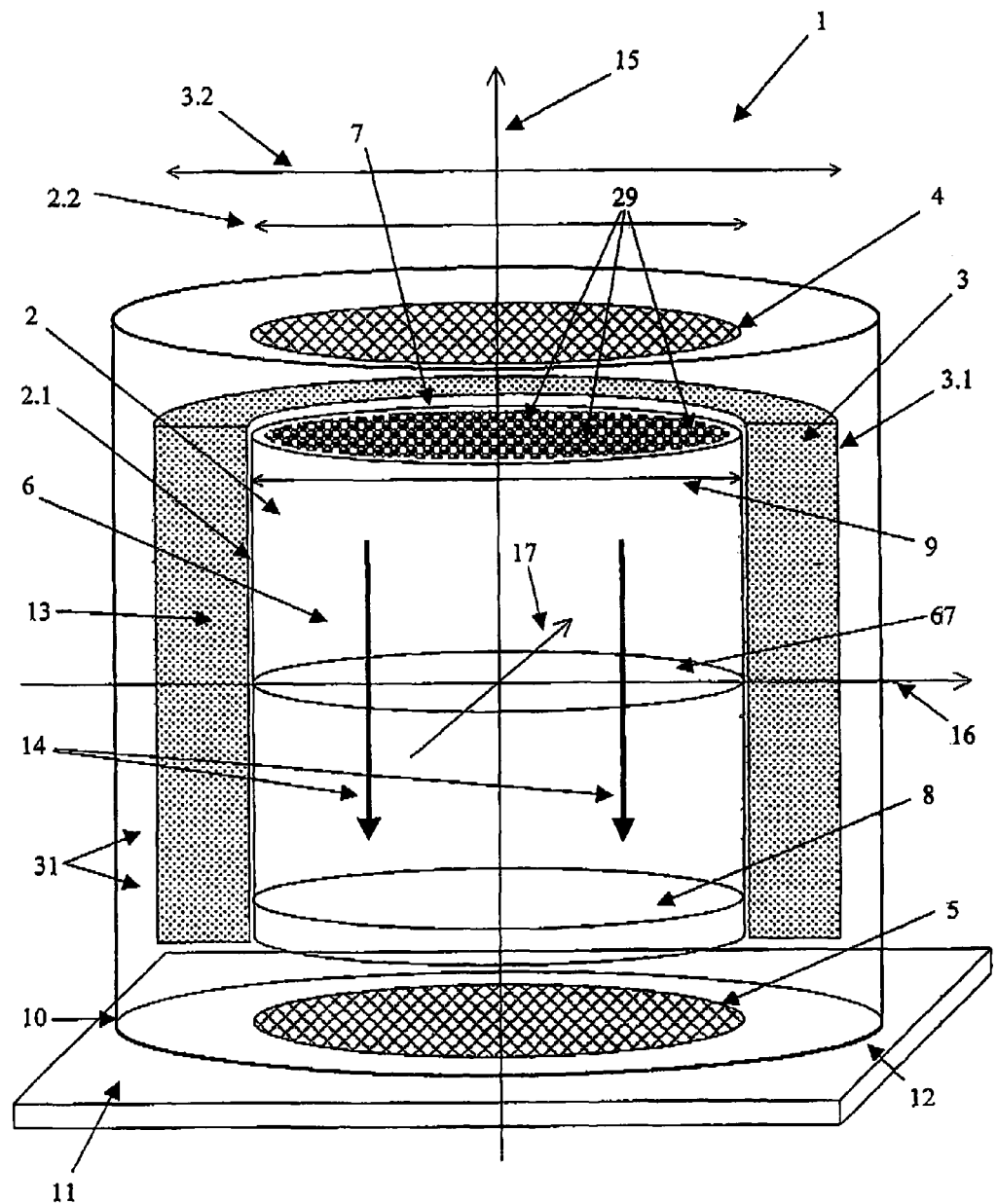
Figure 3:
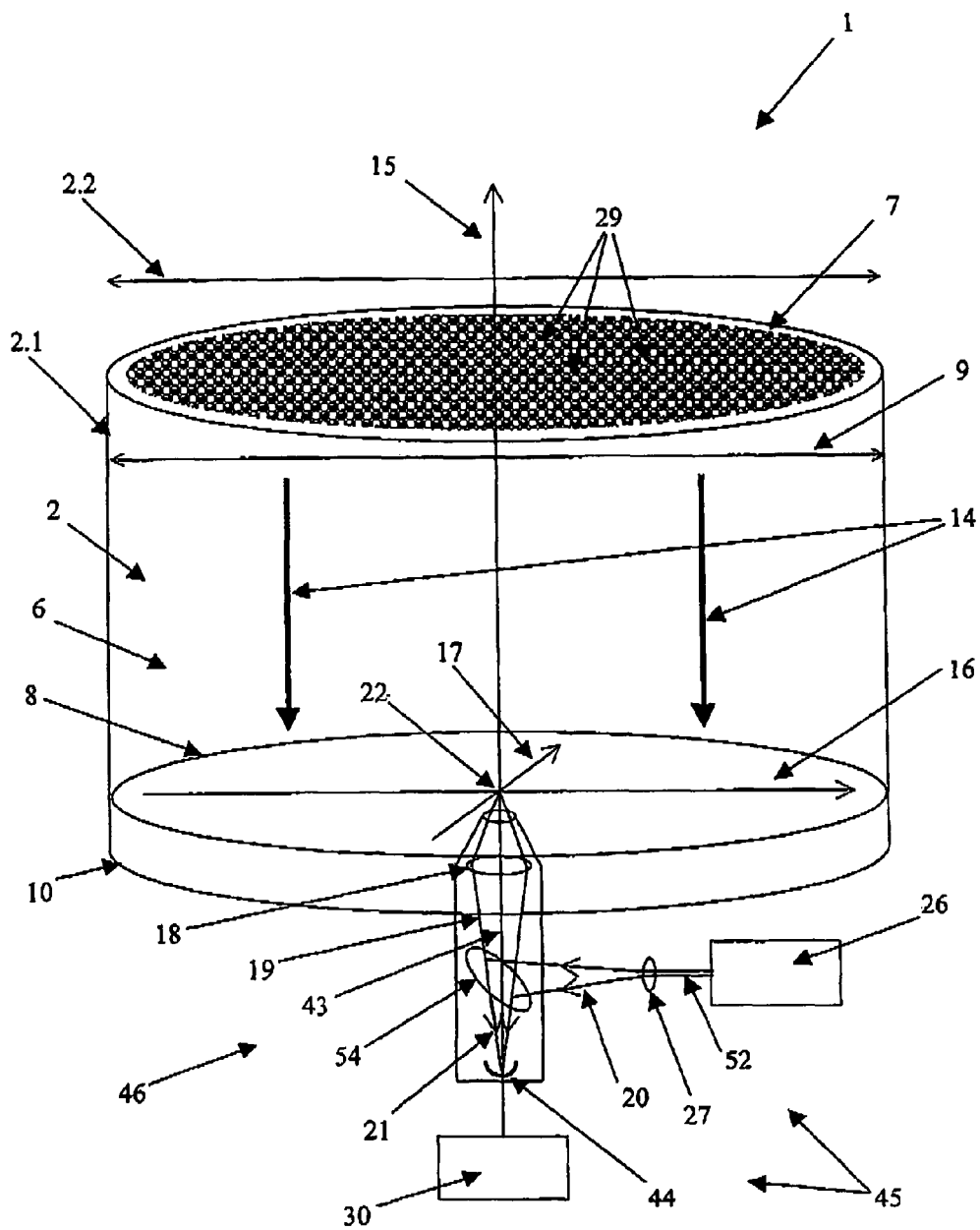
Figure 4:
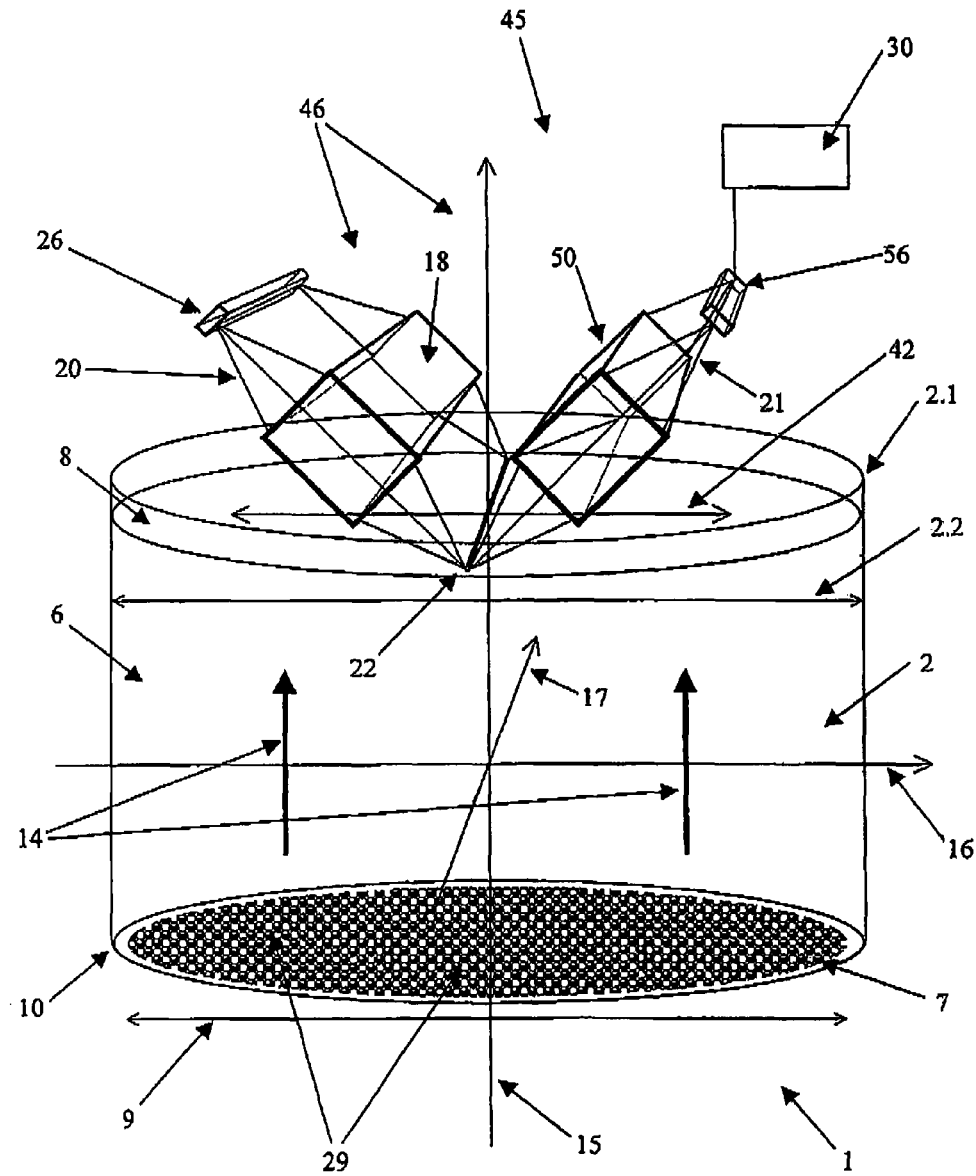
Figure 5:
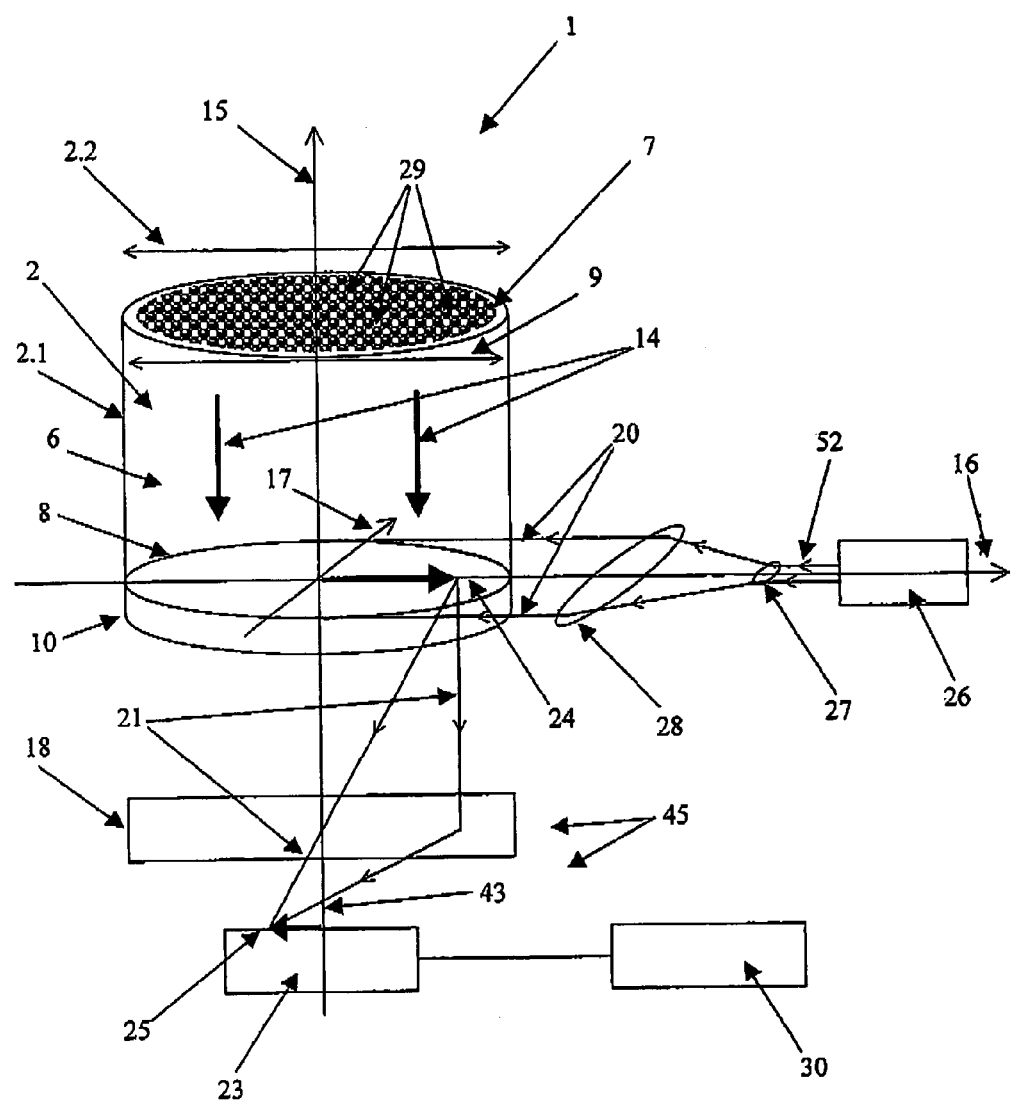
Figure 6:
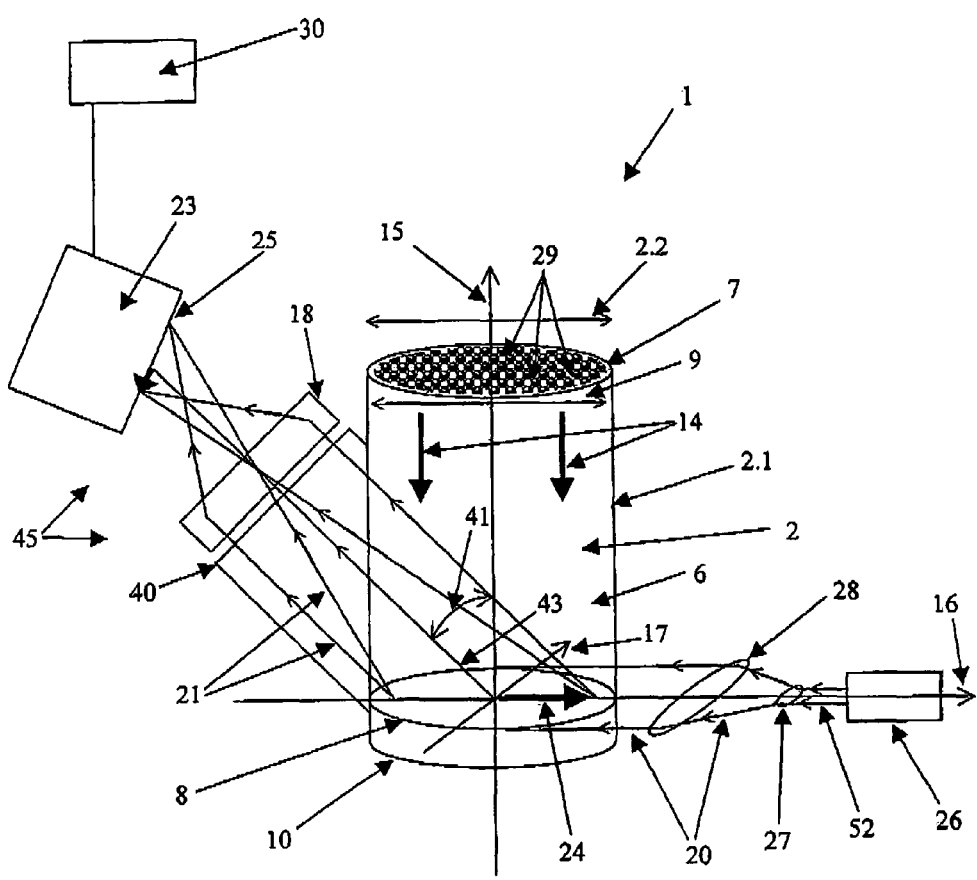
Figure 7:
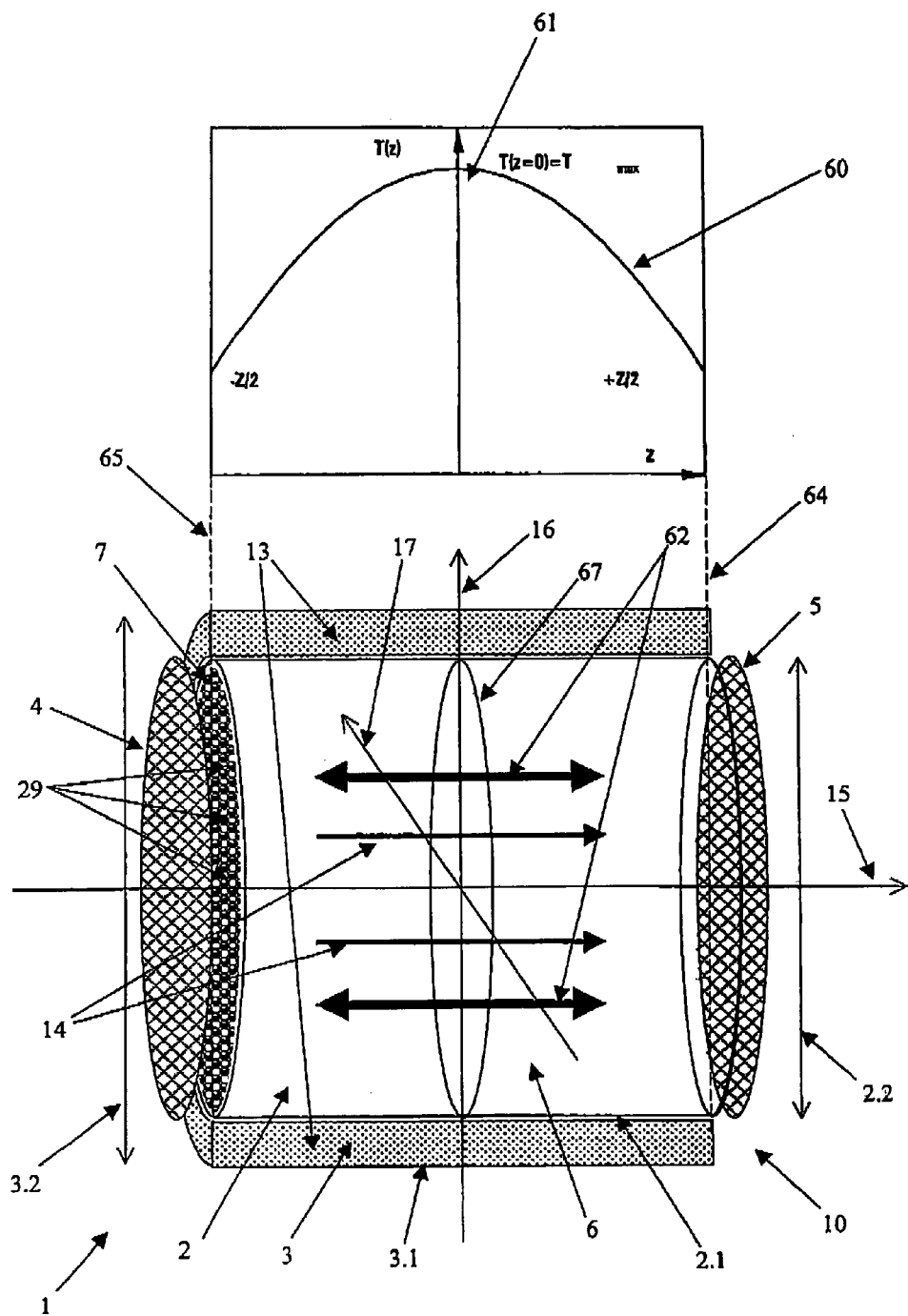

The process proposed according to the invention is illustrated in more detail on the basis of the drawings in which FIG. 1 depicts the principle structure of a fractionating arrangement (separation apparatus) having a hollow space for receiving a separation medium containing an arrangement of samples, FIG. 2 depicts the diagrammatic structure of an (electrophoretic) separation apparatus arranged between two electrodes and having concentric spaces for receiving an insulation and a buffer medium, FIG. 3 depicts the diagrammatic representation of a separation apparatus having a movable measuring head with an illumination apparatus and a detection apparatus in a spot-confocal arrangement and an optical axis which is essentially parallel to the vertical axis (z axis), FIG. 4 depicts the diagrammatic representation of a separation apparatus having a movable measuring head with an illumination apparatus and a detection apparatus in an orthogonal cylindrical-confocal arrangement, FIG. 5 depicts the diagrammatic representation of a separation apparatus having a laterally arranged illumination apparatus and a stationary detector with an optical axis which is essentially parallel to the vertical axis (z axis), FIG. 6 depicts the diagrammatic representation of a separation apparatus having a laterally arranged illumination apparatus and a stationary detector with an optical axis which is essentially tilted with respect to the vertical axis (z axis), and FIG. 7 depicts the directions of heat transfer which are forming on a diagrammatically represented electrophoretic separation apparatus comprising two concentric spaces and the temperature profile which is forming.

FIG. 1 depicts the principle structure of a separation apparatus 1 having a hollow space for receiving the separation medium 6 and a sample plate 7.

The arrangement of a separating structure 1, diagrammatically represented in FIG. 1, comprises a first space 2 serving as an analytic space. The first space 2 is preferably arranged concentrically to the vertical axis (z axis) indicated by reference number 15. The first space 2 is enclosed by a space boundary 2.1 and separated from the surrounding area and designed so as to be able to receive a separation medium 6. The first space 2 has received a separation medium 6 which may be solid, liquid or colloidal, depending on the application. The separation medium 6 may be transparent or non-transparent; the separation medium 6 may be, for example, polyacrylamide, agarose or hydroxylcellulose.

The radius of the first space 2, indicated by 2.2, is preferably in a range between 2 and 15 cm, while the longitudinal extension of the first space 2 in the direction of the z axis 15 may be in the range between 2 cm and 30 cm.

A sample plate 7 which enables a multiplicity of individual samples 29 to be applied is arranged in the separating structure 1 according to the drawing in FIG. 1 above the upper end side of the cylinder arrangement 10 formed by the first space 2 together with its space boundary 2.1. The individual samples 29 are applied essentially two-dimensionally, i.e. the positions of the individual samples 29 on the sample plate 7 may be indicated essentially by two (Cartesian) coordinates, for example in the direction of the x axis 16 and the y axis 17. The distance from the individual samples 29 received on the sample plate 7 to the individual samples adjacent to them is in the range of a few millimeters, preferably below 5 mm. The axial extension 7.1 of the sample plate 7, in the direction of the z axis 15, is small compared to the longitudinal extension of the first space 2, i.e. the analytical space.

The radial extension 9 of the sample plate 7, i.e. its extending perpendicularly to the z axis 15, corresponds preferably to the diameter 2.2 of the first space 2.

Under the influence of a physical or chemical parameter, the individual samples migrate in the direction of the direction of sample migration 14 which is essentially parallel to the z axis 15 (vertical axis) of the separating structure 1, through the separation medium 6 received by the first space 2. The individual samples 29 can be induced to migrate through the separation medium 6, for example, by way of electric forces, gravity forces, via diffusion, pressure or concentration gradients, via osmosis or centrifugal forces.

The separating structure 1 is designed so as to be able to apply the above-mentioned physical or chemical parameters individually or in combination.

In order to (electrophoretically) separate the individual samples 29 by means of electric forces, it is possible, for example, to assign a first electrode element 4 and a second electrode element 5 which have preferably a plate-shaped design to the end sides of the first space 2 serving as an analytical hollow space (cf. FIG. 2).

FIG. 2 depicts diagrammatically the structure of a separation apparatus 1 arranged between two electrode elements 4, 5, which has two spaces received concentrically to one another for receiving a separation medium 6 and an insulation 13 and also a reservoir for receiving a buffer medium 31. The reservoir may be formed by a concentrically received, further space 12, as diagrammatically represented in FIG. 2, for example.

The two spaces 2 and 3 received concentrically to one another and the reservoir form a cylinder arrangement 10 whose end sides are bounded by the electrode elements 4 and 5 which are preferably configured in a plate-shaped manner. The electrode elements 4 and 5 cover the end sides of the first space 2 serving as an analytical hollow space and, where appropriate, also the end sides of the second space 3.

Each of the electrode elements 4 and 5 comprises electrically conductive connections. Said electrically conductive connections may include, for example, a mesh which is received on those sides of the electrode elements 4 and 5, which face the first space 2, i.e. the space containing the separation medium 6. The mesh may preferably be manufactured from a corrosion-resistant, electrically conductive material such as platinum, for example.

When applying an electric voltage to the electrode elements 4 and 5, the individual samples 29 migrate in the direction of sample migration 14 from the electrode element 4 toward the electrode element 5 through the separation medium 6, and are fractionated in the process according to their electrophoretic mobility.

The second space 3 which encloses the first space 2 and is concentrically arranged thereto may receive an insulation 13 which completely surrounds the space boundary 2.1 of the first space and which stops the radial heat exchange perpendicularly to the z axis 15. This results in said space 2 containing the separation medium 6 in the formation of a temperature profile which is independent of a radial (r) coordinate and which has a gradient exclusively in the direction of the z axis 15 and only an insubstantial decrease in temperature in the radial direction (cf. FIG. 7). Consequently, the Joulean heat generated during electrophoresis dissipates according to the separating structure 1 diagrammatically represented in FIG. 2 only via the end sides of the first space 2. Under the idealizing assumption of a heat transport caused only by heat conduction and of a homogeneous electric conductivity of the separation medium 6, a temperature profile is forming in the latter, which depends exclusively on the z coordinate and which follows the quadratic relation depicted below:

$$T(z) = T_{max} - az^2$$

The maximum temperature $T_{max}$, reference number 61, is usually present in a central plane 67 in the center of the cylinder arrangement 10, which is the area at coordinate z=0, spanned by the x axis 16 and the y axis 17. The fact that there is no temperature gradient in the radial (r) direction in the separating structure 1 proposed according to the invention, is the precondition for an isotropic viscosity of the separation medium 6 and a uniform ion mobility forming in the radial direction, based on the vertical axis (z axis 15) of the first space 2. As a result, the migration tracts along which the individual samples 29 migrate through the separation medium 6 in the direction of sample migration 14 run essentially parallel to the z axis 15 without radial deviations.

The second space 3 may in addition be connected to a reservoir which may surround the former as a further space 12 in a concentric arrangement. The buffer medium 31 may be exchanged between the reservoir 12 and the second space 3 via a suitable connection, thereby supporting the setting and maintenance of the electrical, physical and chemical properties of the buffer medium 31 contained in the second space 3. Moreover, the buffer medium 31 can act supportively on setting or maintaining the physical, chemical and electrical properties of the separation medium 6 contained in the first space 2.

The buffer medium 31 (usually a liquid solution) may preferably serve to remove, by means of a thermostatic device provided in or at the reservoir, the Joulean heat being released in the course of the electrophoretic separation process.

The exchange of the buffer medium 31 between the second space 3 and the reservoir may be assisted by a circulating apparatus, for example a pump.

FIG. 3 depicts in a diagrammatic representation a separation apparatus 1 with assigned (online) detection apparatus 45 having a movable measuring head 46 with an optical axis 43 essentially parallel to the z axis 15 and spot-confocal arrangement of the illumination device and the detection device.

The detection apparatus 45 depicted diagrammatically in FIG. 3 is a spot-confocal detection apparatus which detects the radiation starting from a focal point 22 located in the detection region 8 and emitting from the end side of the cylinder arrangement 10. In order to scan the entire area of the detection region 8 of the first space 2, the detection apparatus 45 may be movable in the direction of the x axis 16 and also in the direction of the y axis 17.

The illumination device assigned to the measuring head 46 comprises a preferably monochromatic, coherent radiation source 26, for example a laser, and optics for coupling said laser into said measuring head 46. The path of the radiation starting from the radiation source 26 is indicated in FIG. 3 by the illumination beam path 20. The laser beam 52, depicted here by way of example, may be expanded in a fan-like manner, for example by a lens 27, and then hits a dichroic beam splitter 54 which deflects it in the direction of an optics 18. The optics 18 is designed so as to focus the illumination radiation 20 with high numerical aperture onto the focal point 22 located in the detection region 8 and, at the same time, to capture a maximum proportion of the radiation coming from the sample fractions present in the focal point 22 and to focus said proportion onto the detector 44. The dichroic beam splitter 54 inserted in the beam path 19 separates the radiation coming from the sample fractions present in the focal point 22 from the illumination radiation 20 in a wavelength-dependent manner and delivers it along the detection beam path 21 to the detector 44. The detector 44 produces a usually electrical signal which corresponds to the received radiation and which can be transferred to a data receiving unit 30.

By means of the detection apparatus 45 it is possible, for example, to determine optical properties, preferably the fluorescence intensity or fluorescence wavelength or the absorption or transmission capability of the individual samples 29. The individual samples 29 contained in the sample plate 7 may be provided with labelling substances, for example with fluorescent dyes, to assist detection.

The advantage of the detection apparatus 45 in the spot-confocal arrangement, diagrammatically represented in FIG. 3, can be perceived in its high spatial resolution capability, in particular in its resolution capability in the direction of the x axis 16 and the y axis 17. One disadvantage of the spot-confocal arrangement is the fact that in each case only radiation starting from a focal point 22 reaches the detector 44 so that the detection apparatus 45 must be shifted in the direction of two coordinates, for example in the direction of the x axis 16 and also in the direction of the y axis 17, in order to scan the entire plane of detection 8.

The detection apparatus 45 may combine a plurality of confocal measuring heads 46 of essentially the same type into a multiple measuring head. This makes it possible to receive simultaneously radiation starting from a plurality of focal points 22 located in the plane of detection 8. This reduces the path length by which the detection apparatus 45 has to be shifted in order to be able to capture the entire plane of detection 8 during scanning.

In the case of fractionating the individual samples 29 by electric forces (electrophoretic separation apparatus, cf. FIG. 2), the measuring head 46 or multiple measuring head of the detection apparatus 45 may be integrated in one of the two electrode elements 4 and 5. In this case, the electrode element 4, 5 is moved along by the measuring head 46 during the scanning movement of the latter. This produces, averaged over long periods of time, a homogeneous electric field in the separation medium 6, which is not distorted by the measuring head 46. This is, inter alia, a requirement for a migration of the individual samples 29 along the direction of sample migration 14 essentially parallel to the z axis 15.

FIG. 4 depicts a diagrammatic representation of a separation apparatus having, assigned thereto and located at the top, an (online) detection apparatus 45 with a measuring head 46 in which the illumination device and the detection device are arranged in an orthogonal cylindrical-confocal manner.

In contrast to the arrangement represented in FIG. 3, in which the detection apparatus 45 is located at the bottom, the detection apparatus 45 assigned to the separating structure 1 represented in FIG. 4 is provided above the cylinder arrangement 10. The sample plate 7 is provided at the opposite end side of the cylinder arrangement 10; starting from the sample plate 7, the individual samples 29 migrate through the separation medium 6 in the direction of sample migration 14. The advantage of the arrangement of a separating structure 1 with a detection apparatus 45 located at the top, which arrangement is represented in FIG. 4, can be seen in the fact that gas bubbles which are produced at the upper electrode element 4 (cf. FIG. 2) when said arrangement is used for electrophoretic separation and which may otherwise impair detection can rise laterally rather than accumulate between the detection region 8 and the detection apparatus 45.

The detection apparatus 45 depicted diagrammatically in FIG. 4 is a cylindrical-confocal arrangement which detects the radiation starting from a focal line 22 located in the detection region 8 and emitting from the end side of the cylinder arrangement 10. In order to scan the entire area of the detection region 8 of the first space 2, the detection apparatus 45 must be able to be shifted in the direction of only one coordinate, in the example of FIG. 4 along the shift direction 42 parallel to the x axis 16.

The illumination device assigned to the measuring head 46 comprises a preferably monochromatic, coherent radiation source 26, which may be designed, for example, as a linear arrangement (array) of laser diodes, and a suitable optics 18 for focusing the radiation onto the focal line 22. The optics 18 contains an arrangement of cylinder lenses, microlenses, or gradient index lenses or a combination of the above elements and is designed so as to focus the illumination radiation coming from the radiation source 26 with high numerical aperture onto the focal line 22 located in the plane of detection 8.

FIG. 4 indicates the path of the radiation starting from the radiation source 26 by way of the illumination beam path 20. The optical axis of the illumination beam path 20 and of the detection beam path 21 are tilted, preferably rectangularly (orthogonally), toward each other and cross each other on the focal line 22 in the detection region 8. Alternatively to a single illumination device, as is depicted diagrammatically in FIG. 4, it is also possible for two or more illumination devices to be assigned to the detection apparatus 45. The optical axes of the illumination beam path 20 of all illumination devices provided and of the detection beam path 21 intersect in the focal line 22.

A suitable optics, in the example of FIG. 4 a gradient index lens field 50, focuses the radiation coming from the sample fractions present in the focal line 22 onto a detector field 56. The properties of said optics are chosen in such a way that the sample fractions present in the focal line 22 are projected onto the detector field 56 with a high numerical aperture and a high spatial selectivity. Optical absorption or interference filters may also be provided in the detection beam path 21, for example for increasing the spectral selectivity in an wavelength-dependent detection. The detector field 56 provided is a line-shaped arrangement of individual detectors, for example photodiodes. The detector field 56 generates a usually electrical signal which corresponds to the incident radiation and which may be delivered to a data receiving unit 30.

The advantage of the detection apparatus 45 in an orthogonal cylindrical-confocal embodiment, diagrammatically represented in FIG. 4, is perceivable in its high spatial resolution capability, in particular in its resolution capability (depth of field) in the direction of the z axis 15. Another advantage of the cylindrical-confocal arrangement is the fact that radiation starting from a focal line 22 reaches in each case the detector field 56 so that the detection apparatus 45 needs to be shifted in the direction of only one coordinate, in the example of FIG. 4 in the direction of the x axis 16, in order to scan the entire detection region 8. As FIG. 4 indicates, the shift direction 42 of the detection apparatus 45 is preferably rectangular to the focal line 22.

The detection apparatus 45 may also combine a plurality of cylindrical-confocal measuring heads 46 of essentially the same type into a multiple measuring head. This makes it possible to receive simultaneously radiation starting from a plurality of focal lines 22 located in the detection region 8. This reduces the path lengths by which the detection apparatus 45 needs to be shifted in order to be able to capture the entire detection region 8 during scanning.

In the case of fractionating the individual samples 29 by electric forces (electrophoretic separation apparatus, cf. FIG. 2), it is, similarly to the spot-confocal measuring head (cf. FIG. 3), also possible for the cylindrical-confocal measuring head or the multiple measuring head of the detection apparatus 45 to be integrated in one of the two electrode elements 4 and 5. In this case, the electrode element 4, 5 is moved along by the measuring head 46 during the scanning movement of the latter. This produces, averaged over long periods of time, a homogeneous electric field in the separation medium 6, which is not impaired by the measuring head 46. This is, inter alia, a requirement for a migration of the individual samples 29 along the direction of sample migration 14 essentially parallel to the z axis 15.

FIG. 5 depicts the diagrammatic representation of a separation apparatus 1 with a laterally arranged illumination apparatus and a stationary detector for two-dimensional image taking, whose optical axis 43 is oriented essentially parallel to the vertical axis (z axis 15) of the cylinder arrangement 10.

An illumination apparatus may be arranged laterally to the cylinder arrangement 10, i.e. in the essentially radial (r) direction to the vertical axis thereof (z axis 15). Radiation starting from a radiation source 26 assigned to said illumination apparatus strikes a device, for example a lens 27, which expands the radiation in a fan-like manner, is collimated by a lens 28 and penetrates the cylinder arrangement 10 essentially perpendicularly to the z axis 15. The beam expanded in a fan-like manner in the direction of the y axis 17 illuminates a detection region 8 which is, in the example of FIG. 5, located within the separation medium 6 close to the end-side interface of the latter, which faces away from the sample plate 7. As an alternative to a cylindrical optical system formed by the lenses 27, 28, the laser beam 52 used for illumination in the example of FIG. 5 may also be expanded in a fan-like manner by means of galvanometric deflection apparatuses or rotating polygonal mirrors.

In order to suppress the usually occurring optical diffraction of the illumination radiation when passing through the separation medium 6, it is possible, in the case of fractionation by means of electric forces (electrophoretic separation apparatus, cf. FIG. 2), to adjust the chemical properties of the buffer medium 31 received in the second space 3, for example the concentration of substances dissolved therein, to the properties of the separation medium 6 received in the first space 2 in an advantageous manner.

A detection apparatus 45 may be received on an end side of the cylinder arrangement 10, preferably on the end side facing away from the sample plate 7. The optical axis 43 of said detection apparatus 45 is essentially parallel to the vertical axis (z axis 15) of the cylinder arrangement 10. In this arrangement, the detection apparatus 45 receives radiation which emits from the end side of the first space 2, i.e. the analytical space.

As the diagrammatic representation of the separating structure 1 according to FIG. 5 additionally indicates, an optics 18 may be arranged at an end side of the cylinder arrangement 10. The imaging properties of the optics 18 are chosen in such a way that the image plane 24 located within the detection region 8 is projected two-dimensionally onto the imaging plane 25 located in the image-taking unit 23 with a high spatial resolution and a high numerical aperture. According to the detection beam path 21 drawn into FIG. 5, a point located in the image plane 24 is projected sharply focused by the optics 18 into the imaging plane 25 at the front of the image-taking unit 23.

If the image plane 24 covers only a subregion of the detection region 8, then the detection apparatus 45 may be shifted relative to the cylinder arrangement 10 in one or two coordinate directions, for example in the direction of the x axis 16 and in the direction of the y axis 17, in order to scan the entire detection region 8.

The image-taking unit 23, for example a high-resolution CCD camera, generates a usually electrical signal which corresponds to the incident radiation and which can be transferred to a data receiving unit 30.

FIG. 6 depicts the diagrammatic representation of a separation apparatus 1 with a laterally arranged illumination apparatus and a stationary detection apparatus 45 with an optical axis 43 essentially tilted with respect to the vertical axis (z axis 15).

In the separation apparatus 1 represented diagrammatically in FIG. 6, the detection apparatus 45 with the assigned image-taking unit 23 and optics 18 is, in contrast to the illustration in FIG. 5, arranged laterally to the cylinder arrangement 10 so that its optical axis 43 is inclined to the z axis 15 of the cylinder arrangement 10 by the angle of inclination 41. In this arrangement, the detection apparatus 45 receives radiation which emits from the cylinder arrangement 10 essentially laterally through a suitable window 40.

Analogously to the illustration of the separation apparatus in FIG. 5, the radiation source 26 with this downstream expanding lens 27 and a collecting lens 28 is still provided essentially laterally of the cylinder arrangement 10. The plane detection region 8 which is illuminated by the illumination apparatus by radiation impinging the cylinder arrangement 10 essentially laterally is oriented essentially perpendicularly to the z axis 15, analogously to the illustration according to FIG. 5.

An image-taking unit 23 with an optics 18 assigned thereto is provided laterally outside the space boundary 2.1 of the first space 2. The imaging properties of the optics 18 are chosen in such a way that the image plane 24 located within the detection region 8 is projected two-dimensionally onto the imaging plane 25 located in the image-taking unit 23 with a high spatial resolution and a high numerical aperture. According to the detection beam path 21 drawn into FIG. 6, the optics 18 projects a point located in the image plane 24 through the window 40 into the imaging plane 25 at the front of the image-taking unit 23 in a sharply focused manner.

If the image plane 24 covers only a subregion of the detection region 8, then the detection apparatus 45 may be shifted relative to the cylinder arrangement 10 in order to scan the entire plane of detection 8.

The image-taking unit 23, for example a high-resolution CCD camera, generates a usually electrical signal which corresponds to the incident radiation and which can be transferred to a data receiving unit 30.

The arrangement of the detection apparatus 45 laterally to the cylinder arrangement 10, depicted diagrammatically in FIG. 6, may preferably be used for detecting samples after the separation process has finished. For this purpose, the first space 2 containing the separation medium 6 and the fractionated sample fractions is shifted with respect to the detection region 8, preferably in the direction of sample migration 14, after the separation process has finished. The detection apparatus 45 can receive synchronously thereto a series of two-dimensional single images which are recorded by the data recording unit 30.

FIG. 7 depicts the directions of heat transport 62 which form at a diagrammatically represented electrophoretic separation apparatus comprising two concentric spaces (cf. FIG. 2) and the temperature profile 60 resulting therefrom which prevails along the z axis 15 of the arrangement.

The first space 2 is enclosed by a further, second space 3 arranged concentrically thereto and forms together with the latter a cylinder arrangement 10. The boundary 2.1 of the first space 2 is indicated by the line running parallel to the z axis 15. The second space 3 may receive an insulation 13 so that no heat exchange in the radial direction between the first space 2 receiving the separation medium 6 and the surrounding area is possible. The spaces 2 and 3 are bounded on their particular end sides by electrode elements 4 and 5, respectively, configured in a plate-shaped manner. Electrically conducting connections are present at the electrode elements 4 and 5 configured in a plate-shaped manner, in order to apply a voltage between the electrode elements 4 and 5, which causes the individual samples 29 to migrate from the sample plate 7 in the direction of sample migration 14 essentially parallel to the z axis 15. The Joulean heat produced in the course of the electrophoretic separation process ideally dissipates exclusively via the end faces of the first space 2 into the surrounding area so that, owing to the lack of a temperature gradient in the radial direction, a direction of heat transport 62, starting from the central plane 67 toward the electrode elements 4 and 5, forms, which is indicated by the double arrows drawn in FIG. 7. This results in the formation of a temperature profile 60, represented in FIG. 7, inside the first space 2, which is characterized by a temperature gradient prevailing only in the direction of the z axis 15. The course of this temperature profile which is characteristic for the electrophoretic separation apparatus proposed according to the invention will be derived briefly below:

The electric power density p within the electrophoretic separating structure 1 (separation apparatus) is given by the scalar product of the electric field vector E and the current density vector j:

$$p = \vec{E} \cdot \vec{j} = [W/m^3].$$

In the case of an ideal thermal insulation in the radial direction and a homogeneous electric conductivity of the separation medium 6, a heat transport forms only in the direction of the direction of heat transport 62 essentially parallel to the z axis 15 of the separating structure 1. In this case, the heat flow density q depends only on the z coordinate and the electric power density p (observed in the stationary state) and is described by the integral over the z axis 15, stated below:

$$\vec{q}(z) = \vec{e}_z \cdot \int_0^z \dot{E}(z') \cdot \dot{j}(z') \, dz'$$

$\dot{q}(z) = [W/m^2]$ heat flow density vector at position z
$\vec{e}_z$ = unit vector in the z direction
$\dot{E}(z') = [V/m]$ electric field vector at position z'
$\dot{j}(z') = [A/m^2]$ current density vector at position z'

From this, it is possible to determine the temperature T(z) which ideally is a function only of the z coordinate by means of the integral stated below:

$$T(z) = T_{max} - k \cdot \int_0^{z_v} \dot{q}(z') \, dz', \quad k = \text{const.}$$

The temperature profile 60 prevailing parallel to the z axis 15 is characterized by a maximum temperature $T_{max}$ 61 in the central plane 67, with the z coordinate=0. Starting from the maximum temperature $T_{max}$ 61, a temperature decrease forms toward both the end sides of the cylinder arrangement 10, i.e. in the direction of an increasing and, respectively, decreasing z coordinate toward the first space end 64 at position +z/2 and, respectively, the second space end 65 at position −z/2. If the electric power density p(z) is assumed to be homogeneous across the entire separation medium 6, then the temperature profile 60 takes the course represented in FIG. 7, which is a function of the square of the z coordinate.

However, in practical applications inhomogeneities may occur, due to inaccuracies, temperature fluctuations or charge distribution fluctuations taking place, and may result in a nonquadratic temperature distribution.

EXAMPLE

A separating structure 1 was tested for separating samples by means of electrophoresis under various experimental conditions. The online detection and data receiving unit used was the prototype of an ARAKIS sequencer. The detection region 8 was illuminated perpendicularly to the direction of sample migration 14) by means of a helium-neon laser with a wavelength of 594=n (yellow) and an optical power of 3 W. Said laser is likewise part of the ARAKIS sequencer.

The separation medium 6 used was a polyacrylamide gel at various concentrations of between 10 and 20%. The separation distance was 6 cm (z direction) and the diameter of the first space 2 receiving the separation medium 6 was likewise 6 cm. Under these conditions, DNA sequencing in a standardized two-dimensional gel produces sequences which are readable over a length of up to 150 bp (bp=base pairs).

The electrophoretic power was limited to 10 W, resulting in a voltage of about 60 V between the electrodes 4, 5. This corresponds to an electric field strength of about 10 V/cm, with a separation distance of 6 cm.

The results obtained with the outlined separating structure 1 under the conditions indicated above showed that DNA fragments reached the detection region within a period of from 4 to 6 hours, without an influence of thermal effects such as, for example, irregular band migration (smiling effect) being noticeable.

However, under the abovementioned conditions, the fractionation of the bands was always below the single base resolution, even when the gel concentration was increased to up to 20%. The provisional manner of detection, the strong diffusion of the samples due to their long migration time in the weak electric field and the exhaustion of buffer capacity occurring after a long migration time are considered to be limiting factors for the separating performance (resolution).

When the separation distance was increased to 10 cm in a modified separating structure 1, it was nevertheless possible to achieve single base resolution. DNA sequencing reactions carried out under these conditions delivered readable DNA sequences of about 50 bp (base pairs) in length, which is considered to be sufficient for identifying genes in the course of expression studies (signature sequencing). The process of the invention is furthermore suitable for simultaneous DNA and protein sequencing reactions of a complex number of individual samples 29 in the course of shotgun sequencing reactions, parallel signature sequencing reactions and for sequencing reactions in the course of protein and expression analysis. The density of the sample application 7 used in the separating structure 1 in the experiments carried out was a 2 mm spacing between the individual samples 29. A higher packing density of the sample application 7 down to spacings of below 1 mm is possible.

List of Reference Numbers

1 Separating structure (separation apparatus)
2 First space (hollow)
2.1 Space boundary
2.2 Diameter of the first space
3 Second space
3.1 Space boundary
3.2 Diameter of the second space
4 First electrode element
5 Second electrode element
6 Separation medium
7 Sample plate
7.1 Axial extension (of the sample plate)
8 Detection region
9 Radial extension (of the sample plate)
10 Cylinder arrangement
11 Bottom
12 Further space (reservoir)
13 Insulation
14 Direction of sample migration
15 z axis
16 x axis
17 y axis
18 Optics
19 Beam path
20 Illumination beam path
21 Detection beam path
22 Focal point/focal line
23 Image-taking unit
24 Image plane
25 Imaging plane
26 Radiation source
27 Lens (for expanding the beam in a fan-like manner)
28 Collecting lens
29 Individual samples
30 Data receiving unit
31 Buffer medium
40 Window
41 Angle of inclination $\alpha$
42 Shift direction
43 Optical axis
44 Detector
45 Detection apparatus
46 (Confocal) measuring head
50 Gradient index lens field
52 Laser beam
54 Dichroic beam splitter
56 Detector field
60 Temperature profile
61 Maximum temperature $T_{max}$
62 Direction of heat transport
64 First space end (+z/2)
65 Second space end (−z/2)
67 Central plane

The invention claimed is:

1. A method for the simultaneous parallel fractionation of a multiplicity of individual samples, the method comprising:
(a) loading the multiplicity of individual samples onto a first surface of a single unit of separation medium, wherein the samples are arranged two-dimensionally with respect to each other on the first surface;
(b) simultaneously separating the individual samples into fractions by migrating the samples through the separation medium in the direction of a third dimension, wherein no physical barrier, except the separation medium, separates the individual samples during their fractionation; and
(c) detecting and/or preparatively collecting the fractioned samples.

2. The method of claim 1, wherein during migration, the individual samples are detected in selected regions within the separation medium or close to an interface of the separation medium.

3. The method of claim 1, wherein separating the individual samples into fractions comprises applying an electrical voltage, and wherein the individual samples migrate through the separation medium essentially perpendicularly to the plane of their loading.

4. The method of claim 1, wherein a temperature distribution is generated and/or maintained within the separation medium, which is essentially independent of a coordinate running perpendicular to the direction of sample migration.

5. The method of claim 1, wherein loading the multiplicity of samples comprises contacting the surface of the separation medium with a sample plate containing the samples in the two-dimensional arrangement.

6. The method of claim 5, wherein the individual samples are arranged on the sample plate according to physical or chemical properties of the individual samples.

7. The method of claim 6, wherein arranging the individual samples on the sample plate comprises a cell sorter or a fluorescence-activated cell sorter (FACS).

8. The method of claim 1, wherein the individual samples comprise amplification products.

9. The method of claim 8, wherein the amplification comprises cloning and subsequent selective propagation.

10. The method of claim 8, wherein the amplification comprises the polymerase chain reaction.

11. The method of claim 5, wherein the individual samples on the sample plate comprise fractions derived from a pre-fractionation of individual sample sources.

* * * * *